United States Patent
Carson et al.

(10) Patent No.: US 8,846,697 B2
(45) Date of Patent: Sep. 30, 2014

(54) PURINE ANALOGS

(75) Inventors: Dennis A. Carson, La Jolla, CA (US); Howard B. Cottam, Escondido, CA (US); Guangyi Jin, Berkeley, CA (US); Christina C. N. Wu, Escondido, CA (US); Kenji Takabayashi, Poway, CA (US); Suzanne Grimshaw, legal representative, Poway, CA (US)

(73) Assignee: The Regents of the University of California, Oakland, CA (US)

( * ) Notice: Subject to any disclaimer, the term of this patent is extended or adjusted under 35 U.S.C. 154(b) by 1246 days.

(21) Appl. No.: 12/302,738

(22) PCT Filed: Apr. 23, 2007

(86) PCT No.: PCT/US2007/009840
§ 371 (c)(1),
(2), (4) Date: Dec. 17, 2010

(87) PCT Pub. No.: WO2007/142755
PCT Pub. Date: Dec. 13, 2007

(65) Prior Publication Data
US 2011/0098294 A1    Apr. 28, 2011

Related U.S. Application Data

(60) Provisional application No. 60/810,184, filed on May 31, 2006.

(51) Int. Cl.
*A61K 31/52*    (2006.01)
*C07D 473/18*    (2006.01)

(52) U.S. Cl.
USPC .................... 514/263.37; 544/276

(58) Field of Classification Search
USPC ............ 544/118, 276, 277; 514/234.2, 263.2, 514/263.22, 263.23, 263.27, 263.4
See application file for complete search history.

(56) References Cited

U.S. PATENT DOCUMENTS

| | | | |
|---|---|---|---|
| 4,689,338 A | 8/1987 | Gerster | |
| 4,929,624 A | 5/1990 | Gerster et al. | |
| 4,938,949 A | 7/1990 | Borch et al. | |
| 5,037,986 A | 8/1991 | Gerster | |
| 5,175,296 A | 12/1992 | Gerster | |
| 5,238,944 A | 8/1993 | Schultz et al. | |
| 5,352,784 A | 10/1994 | Nikolaides et al. | |
| 5,367,076 A | 11/1994 | Gerster | |
| 5,395,937 A | 3/1995 | Nikolaides et al. | |
| 5,444,065 A | 8/1995 | Nikolaides et al. | |
| 5,624,677 A | 4/1997 | El-Rashidy et al. | |
| 5,627,281 A | 5/1997 | Nikolaides et al. | |
| 5,648,516 A | 7/1997 | Nikolaides et al. | |
| 5,693,811 A | 12/1997 | Lindstrom | |
| 5,736,553 A | 4/1998 | Wick et al. | |
| 5,741,908 A | 4/1998 | Gerster et al. | |
| 5,998,619 A | 12/1999 | Gerster et al. | |
| 6,038,505 A | 3/2000 | Probst et al. | |
| 6,039,969 A | 3/2000 | Tomai et al. | |
| 6,083,505 A | 7/2000 | Miller et al. | |
| 6,150,523 A | 11/2000 | Gerster et al. | |
| 6,200,592 B1 | 3/2001 | Tomai et al. | |
| 6,245,776 B1 | 6/2001 | Skwiercynski et al. | |
| 6,329,381 B1 | 12/2001 | Kurimoto et al. | |
| 6,333,331 B1 | 12/2001 | Moschel et al. | |
| 6,372,725 B1 | 4/2002 | Zilch et al. | |
| 6,437,131 B1 | 8/2002 | Gerster et al. | |
| 6,486,168 B1 | 11/2002 | Skwierczynski et al. | |
| 6,534,654 B2 | 3/2003 | Gerster et al. | |
| 6,552,192 B1 | 4/2003 | Hanus et al. | |
| 6,610,319 B2 | 8/2003 | Tomai et al. | |
| 6,613,902 B2 | 9/2003 | Gerster et al. | |
| 6,624,305 B2 | 9/2003 | Gerster | |

(Continued)

FOREIGN PATENT DOCUMENTS

| | | |
|---|---|---|
| AU | 2007257423 | 5/2012 |
| EP | 0145340 A2 | 6/1985 |
| EP | 0310950 A1 | 4/1989 |
| EP | 0389302 A1 | 9/1990 |
| EP | 0394026 A1 | 10/1990 |
| EP | 0553202 A1 | 8/1993 |
| EP | 0575549 A1 | 12/1993 |
| EP | 0636031 A1 | 2/1995 |
| EP | 0681570 A1 | 11/1995 |
| EP | 0708773 A1 | 5/1996 |

(Continued)

OTHER PUBLICATIONS

Butler, Journal of Materials Chemistry 17(19), 1863-1865 (Feb. 26, 2007).*

(Continued)

*Primary Examiner* — Golam M M Shameem
*Assistant Examiner* — Laura Daniel
(74) *Attorney, Agent, or Firm* — Schwegman Lundberg & Woessner, P.A.

(57) ABSTRACT

The present invention provides purine analog compounds, as well as compositions and methods of using them, for example, to prevent or treat various diseases and disorders in human and non-human animals. For example, the invention provides for a compound having formula II:

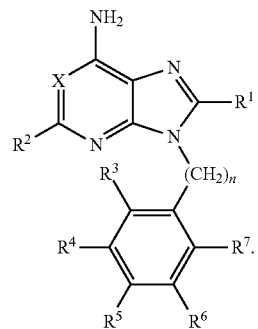

13 Claims, No Drawings

(56) References Cited

U.S. PATENT DOCUMENTS

| | | |
|---|---|---|
| 6,696,076 B2 | 2/2004 | Tomai et al. |
| 6,706,728 B2 | 3/2004 | Hedenstrom et al. |
| 6,716,840 B2 | 4/2004 | Chu et al. |
| 6,733,764 B2 | 5/2004 | Martin |
| 6,734,187 B1 | 5/2004 | Tanaka et al. |
| 6,897,314 B2 | 5/2005 | Gerster et al. |
| 6,960,582 B2 | 11/2005 | Boyce et al. |
| 7,001,609 B1 | 2/2006 | Matson et al. |
| 7,157,465 B2 | 1/2007 | Isobe et al. |
| 7,189,727 B2 | 3/2007 | Boyce |
| 7,238,700 B2 * | 7/2007 | Palle et al. ............... 514/263.4 |
| 7,241,890 B2 | 7/2007 | Kasibhatla et al. |
| 7,521,454 B2 | 4/2009 | Isobe et al. |
| 7,754,728 B2 | 7/2010 | Isobe et al. |
| 7,968,544 B2 | 6/2011 | Graupe et al. |
| 8,357,374 B2 | 1/2013 | Carson et al. |
| 8,729,088 B2 | 5/2014 | Carson et al. |
| 8,790,655 B2 | 7/2014 | Carson |
| 2002/0127224 A1 | 9/2002 | Chen |
| 2002/0193595 A1 | 12/2002 | Chu et al. |
| 2003/0187261 A1 | 10/2003 | Havlicek et al. |
| 2003/0191086 A1 | 10/2003 | Hanus et al. |
| 2004/0023211 A1 | 2/2004 | Groen et al. |
| 2004/0132748 A1 | 7/2004 | Isobe et al. |
| 2004/0209899 A1 * | 10/2004 | Palle et al. ............... 514/263.2 |
| 2004/0248895 A1 | 12/2004 | Chu et al. |
| 2004/0265351 A1 | 12/2004 | Miller et al. |
| 2005/0004144 A1 | 1/2005 | Carson et al. |
| 2005/0038027 A1 | 2/2005 | Boyce |
| 2005/0049263 A1 | 3/2005 | Kasibhatla et al. |
| 2005/0054590 A1 | 3/2005 | Averett |
| 2005/0059613 A1 | 3/2005 | Memarzadeh et al. |
| 2005/0266067 A1 | 12/2005 | Sengupta et al. |
| 2006/0052403 A1 | 3/2006 | Isobe et al. |
| 2006/0110746 A1 | 5/2006 | Andre et al. |
| 2007/0037832 A1 | 2/2007 | Isobe et al. |
| 2007/0087009 A1 | 4/2007 | Burdin |
| 2007/0100146 A1 | 5/2007 | Dzwiniel |
| 2007/0161582 A1 | 7/2007 | Mijikovic et al. |
| 2007/0173483 A1 | 7/2007 | Kasibhatla et al. |
| 2007/0190071 A1 | 8/2007 | Kurimoto et al. |
| 2007/0292418 A1 | 12/2007 | Fields et al. |
| 2008/0008682 A1 * | 1/2008 | Chong et al. ............... 424/85.6 |
| 2008/0125446 A1 | 5/2008 | Kasibhatla et al. |
| 2008/0214580 A1 | 9/2008 | Neagu et al. |
| 2009/0047249 A1 | 2/2009 | Graupe et al. |
| 2009/0069289 A1 | 3/2009 | Neagu et al. |
| 2009/0099212 A1 * | 4/2009 | Zablocki et al. ........... 514/263.2 |
| 2009/0105212 A1 | 4/2009 | Isobe et al. |
| 2009/0118263 A1 | 5/2009 | Hashimoto et al. |
| 2009/0202484 A1 | 8/2009 | Chong et al. |
| 2009/0202626 A1 | 8/2009 | Carson et al. |
| 2009/0324551 A1 | 12/2009 | Carson et al. |
| 2010/0210598 A1 | 8/2010 | Carson et al. |
| 2011/0098248 A1 | 4/2011 | Halcomb et al. |
| 2011/0319442 A1 | 12/2011 | Leoni et al. |
| 2012/0003298 A1 | 1/2012 | Barberis et al. |
| 2012/0009247 A1 | 1/2012 | Maj et al. |
| 2012/0083473 A1 | 4/2012 | Holldack et al. |
| 2012/0148660 A1 | 6/2012 | Carson et al. |
| 2012/0177681 A1 * | 7/2012 | Singh et al. ............... 424/193.1 |
| 2013/0156807 A1 | 6/2013 | Carson et al. |
| 2013/0165455 A1 | 6/2013 | Carson et al. |
| 2013/0190494 A1 | 7/2013 | Carson et al. |

FOREIGN PATENT DOCUMENTS

| | | |
|---|---|---|
| EP | 0912564 A1 | 5/1999 |
| EP | 0912565 A1 | 5/1999 |
| EP | 0938315 A1 | 9/1999 |
| EP | 1035123 A1 | 9/2000 |
| EP | 1386923 A1 | 2/2004 |
| EP | 1550662 A1 | 7/2005 |
| EP | 1939202 A1 | 7/2008 |
| JP | 2004-137157 A | 5/2004 |
| JP | 2005-089334 A | 4/2005 |
| WO | WO-9215581 A1 | 9/1992 |
| WO | WO-9320847 A1 | 10/1993 |
| WO | WO-9817279 A1 | 4/1998 |
| WO | WO-9848805 A1 | 11/1998 |
| WO | WO-99/28321 A1 | 6/1999 |
| WO | WO-00/43394 A1 | 7/2000 |
| WO | WO-01/44259 A1 | 6/2001 |
| WO | WO-01/44260 A2 | 6/2001 |
| WO | WO-0149688 A1 | 7/2001 |
| WO | WO-0224225 A1 | 3/2002 |
| WO | WO-03077944 A1 | 9/2003 |
| WO | WO-2005025583 A2 | 3/2005 |
| WO | WO-2005060966 A1 | 7/2005 |
| WO | WO-2005/092892 A1 | 10/2005 |
| WO | WO-2006100226 A1 | 9/2006 |
| WO | WO-2007/034817 A1 | 3/2007 |
| WO | WO-2007/034917 A1 | 3/2007 |
| WO | WO-2007024707 A2 | 3/2007 |
| WO | WO-2007024707 A3 | 3/2007 |
| WO | WO-2007/038720 A2 | 4/2007 |
| WO | WO-2007142755 A2 | 12/2007 |
| WO | WO-2007142755 A3 | 12/2007 |
| WO | WO-2008115319 A2 | 9/2008 |
| WO | WO-2008115319 A3 | 9/2008 |
| WO | WO-2009005687 A1 | 1/2009 |
| WO | WO-2009099650 A2 | 8/2009 |
| WO | WO-2009099650 A3 | 8/2009 |
| WO | WO-2009099650 A4 | 8/2009 |
| WO | WO-2010093436 A2 | 8/2010 |
| WO | WO-2011/139348 A2 | 11/2011 |

OTHER PUBLICATIONS

"Australian Application Serial No. 2007257423, First Examiner Report mailed Sep. 22, 2010", 4 Pgs.

"Canadian Application Serial No. 2,653,941, Office Action Received mailed Aug. 23, 2010", 5 pgs.

Dolan, M. E, et al., "Metabolism of O6-benzylguanine, an inactivator of O6-alkylguanine-DNA alkyltransferase.", Cancer Res., 54(19), (Oct. 1, 1994), 5123-30.

Jin, G., et al., "Synthesis and immunostimulatory activity of 8-substituted amino 9-benzyladenines as potent Toll-like receptor 7 agonists.", Bioorg Med Chem Lett., 16(17), (Sep. 1, 2006), 4559-63.

"U.S. Appl. No. 12/027,960, Response to Rule 312 Communication mailed Nov. 14, 2012", 2 pgs.

"U.S. Appl. No. 12/027,960, Non Final Office Action mailed Apr. 10, 2012", 16 pgs.

"U.S. Appl. No. 12/027,960, Notice of Allowance mailed Aug. 1, 2012", 11 pgs.

"U.S. Appl. No. 12/027,960, Response filed Jul. 10, 2012 to Non Final Office Action mailed Apr. 10, 2012", 8 pgs.

"U.S. Appl. No. 12/027,960, Response filed Oct. 24, 2011 to Restriction Requirement mailed Sep. 23, 2011", 21 pgs.

"U.S. Appl. No. 12/027,960, Restriction Requirement mailed Sep. 23, 2011", 9 pgs.

"U.S. Appl. No. 12/064,529 , Response filed Jul. 9, 2012 to Non Final Office Action mailed Apr. 9, 2012", 11 pgs.

"U.S. Appl. No. 12/064,529, Final Office Action mailed Sep. 20, 2012", 14 pgs.

"U.S. Appl. No. 12/064,529, Non Final Office Action mailed Apr. 9, 2012", 15 pgs.

"U.S. Appl. No. 12/064,529, Response filed Oct. 24, 2011 to Restriction Requirement mailed Aug. 24, 2011", 9 pgs.

"U.S. Appl. No. 12/064,529, Restriction Requirement mailed Aug. 24, 2011", 9 pgs.

"U.S. Appl. No. 12/367,172 , Response filed Aug. 13, 2012 to Final Office Action mailed Apr. 13, 2012", 9 pgs.

"U.S. Appl. No. 12/367,172, Final Office Action mailed Jan. 18, 2012", 15 pgs.

"U.S. Appl. No. 12/367,172, Final Office Action mailed Apr. 13, 2012", 21 pgs.

"U.S. Appl. No. 12/367,172, Response filed Mar. 8, 2011 to Restriction Requirement mailed Dec. 8, 2010", 11 pgs.

(56) References Cited

OTHER PUBLICATIONS

"U.S. Appl. No. 12/367,172, Response filed Nov. 16, 2011 to Non Final Office Action mailed May 27, 2011", 6 pgs.
"U.S. Appl. No. 12/704,343, Non Final Office Action mailed Jul. 16, 2012", 14 pgs.
"U.S. Appl. No. 12/704,343, Response filed Jun. 5, 2012 to Restriction Requirement mailed May 7, 2012", 7 pgs.
U.S. Appl. No. 12/704,343, Response filed Oct. 16, 2012 to Non Final Office Action mailed Jul. 16, 2012, 12 pgs.
"U.S. Appl. No. 12/704,343, Restriction Requirement mailed May 7, 2012", 7 pgs.
"Australian Application Serial No. 2007257423, Examiner Report mailed Jun. 6, 2011", 2 pgs.
"Australian Application Serial No. 2007257423, Office Action mailed Oct. 20, 2011", 2 pgs.
"Australian Application Serial No. 2007257423, Response filed May 31, 2011 to First Examiner Report mailed Sep. 22, 2010", 16 pgs.
"Australian Application Serial No. 2007257423, Response filed Sep. 13, 2011 to Examination Report mailed Jun. 6, 2011", 12 pgs.
"Australian Application Serial No. 2007257423, Response filed Dec. 19, 2011 to Office Action mailed Oct. 20, 2011", 5 pgs.
"Canadian Application Serial No. 2,653,941, Office Action May 10, 2011", 3 pgs.
"Canadian Application Serial No. 2,653,941, Office Action mailed Feb. 8, 2012", 2 pgs.
"Canadian Application Serial No. 2,653,941, Response filed Aug. 2, 2012 to Office Action mailed Feb. 8, 2012", 7 pgs.
"Canadian Application Serial No. 2,653,941, Response filed Nov. 9, 2011 to Office Action mailed May 10, 2011", 15 pgs.
"European Application Serial No. 07755916.9, Office Action mailed Nov. 11, 2011", 1 pg.
"European Application Serial No. 07755916.9, Response filed May 18, 2012 to Extended Search Report mailed Oct. 25, 2011", 11 pgs.
"European Application Serial No. 07755916.9, Supplemental Search Report mailed Oct. 25, 2011", 9 pgs.
"I. Pharmaceutical Importance of Crystallin Hydrates", [online]. [retrieved on May 30, 2008]. Retrieved from the Internet: <URL: http://www.netlibrary.com/nlreader.dll?bookid=12783 &filename=Page_126.html>, (2008), 126-127.
Carson, D. A., et al., "TLR Agonists", U.S. Appl. No. 60/710,337, filed Aug. 22, 2005, 52 pgs.
"U.S. Appl. No. 12/027,960, Preliminary Amendment mailed Dec. 8, 2010", 21 pgs.
"U.S. Appl. No. 12/367,172, Non Final Office Action mailed May 27, 2011", 20 pgs.
"U.S. Appl. No. 12/367,172, Restriction Requirement mailed Dec. 8, 2010", 6 pgs.
"Australian Application Serial No. 2006283524, Office Action mailed Mar. 27, 2008", 1 pg.
"Australian Application Serial No. 2006283524, Preliminary Amendment mailed Mar. 3, 2008", 18 pgs.
"Australian Application Serial No. 2006283524, Response filed May 19, 2008 to Office Action mailed Mar. 27, 2008", 10 pgs.
"Australian Application Serial No. 2008227128, Preliminary Amendment filed Sep. 7, 2009", 45 pgs.
"Brazilian Application Serial No. PI 0807196-9, Amendment filed Mar. 2, 2011", 13 pgs.
"Canadian Application Serial No. 2,653,941, Response filed Feb. 23, 2011 to Office Action Received mailed Aug. 23, 2010", 20 pgs.
"Chinese Application Serial No. 200680038761.X, Office Action mailed Apr. 14, 2010", with English translation, 9 pgs.
"Chinese Application Serial No. 200680038761.X, Office Action Response Filed Oct. 29, 2010", with English translation of amended claims, 22 pgs.
"Chinese Application Serial No. 200880011525.8, Voluntary Amendment filed Dec. 2, 2010", (w/ English Translation of Claims), 12 pgs.
"Chinese Application Serial No. 200980112411.7, Voluntary Amendment filed Jan. 31, 2011", (w/ English Translation of Claims), 74 pgs.

"Eurasian Application Serial No. 200901078, Office Action mailed May 26, 2011", 3 pgs.
"European Application Serial No. 06813535.9, Voluntary Amendment filed Apr. 22, 2008", 9 pgs.
"European Application Serial No. 08799591.6, Office Action mailed Jun. 4, 2010", 4 pgs.
"European Application Serial No. 08799591.6, Office Action Response Filed Dec. 2, 2010", 20 pgs.
"European Application Serial No. 09709019.5, Extended European Search Report mailed Feb. 15, 2011", 8 pgs.
"European Application Serial No. 08799591.6, Examination Notification Art. 94(3) mailed May 17, 2011", 5 pgs.
"International Application Serial No. PCT/US06/32371, International Search Report mailed Jul. 23, 2007", 3 pgs.
"International Application Serial No. PCT/US06/32371, Written Opinion mailed Jul. 23, 2007", 6 pgs.
"International Application Serial No. PCT/US2007/009840, International Preliminary Report On Patentability mailed Dec. 18, 2008", 9 pgs.
"International Application Serial No. PCT/US2008/001631, International Preliminary Examination Report mailed Aug. 20, 2009", 12 pgs.
"International Application Serial No. PCT/US2008/001631, International Search Report mailed Jan. 21, 2009", 6 pgs.
"International Application Serial No. PCT/US2008/001631, Voluntary Amendment filed Aug. 7, 2009", 45 pgs.
"International Application Serial No. PCT/US2008/001631, Written Opinion mailed Jan. 21, 2009", 9 pgs.
"International Application Serial No. PCT/US2009/000771, International Search Report mailed Aug. 28, 2009", 4 pgs.
"International Application Serial No. PCT/US2009/000771, Written Opinion mailed Aug. 28, 2009", 5 pgs.
"International Application Serial No. PCT/US2010/000369, International Search Report mailed Sep. 21, 2010", 6 pgs.
"International Application Serial No. PCT/US2010/000369, Partial International Search Report mailed Jul. 5, 2010", 6 pgs.
"International Application Serial No. PCT/US2010/000369, Written Opinion mailed Feb. 11, 2010", 9 pgs.
"International Application Serial No. PCT/US2010/000369, Written Opinion mailed Sep. 21, 2010", 9 pgs.
"Japanese Application Serial No. 2008-528017, Preliminary Amendment filed Aug. 12, 2009", 26 pgs.
"Japanese Application Serial No. 2010-545884, Voluntary Amendment filed Oct. 7, 2010", 65 pgs.
Baenziger, S., et al., "Triggering TLR7 in mice induces immune activation and lymphoid system disruption, resembling HIV-mediated pathology", Blood, 113(2), (Jan. 8, 2009), 377-388.
Bryan, G. T., et al., "Interferon (IFN) and IFN Inducers Protect Mouse Bladder Urothelium Against Carcinogenicity by FANFT", Journal of Cancer Research and Clinical Oncology, 116(Suppl. Part 1), (Abstract A3.106.36), (15th International Cancer Congress, Hamburg, Aug. 16-22, 1990), (1990), p. 308.
Chan, M., et al., "Synthesis and immunological characterization of toll-like receptor 7 agonistic conjugates", Bioconjug Chem., 20(6), (Jun. 2009), 1194-200.
Colombo, R., et al., "Combination of intravesical chemotherapy and hyperthermia for the treatment of superficial bladder cancer: preliminary clinical experience", Crit Rev Oncol Hematol., 47(2), (Aug. 2003), 127-39.
Hayashi, T., et al., "Mast cell-dependent anorexia and hypothermia induced by mucosal activation of Toll-like receptor 7", Am J Physiol Regul Integr Comp Physiol., 295(1), (2008), R123-32.
Kobayashi, H., et al., "Prepriming: a novel approach to DNA-based vaccination and immunomodulation", Springer Seminars in Immunopathology, 22(Nos. 1-2), (2000), 85-96.
Kulikov, V. I, et al., "Lipid derivatives of prostaglandins and nonsteroidal antiinflammatory drugs (a review)", Pharmaceutical Chemistry Journal, 31(4), (1997), 173-177.
Kurimoto, A., et al., "Synthesis and structure-activity relationships of 2-amino-8-hydroxyadenines as orally active interferon inducing agents", Bioorg Med Chem., 11(24), (Dec. 1, 2003), 5501-8.

(56) References Cited

OTHER PUBLICATIONS

Lee, J., et al., "Molecular basis for the immunostimulatory activity of guanine nucleoside analogs: Activation of Toll-like receptor 7", Proc. Natl. Acad. Sci., 100(11), (2003), 6646-6651.

Liu, H., et al., "Tumour growth inhibition by an imidazoquinoline is associated with c-Myc down-regulation in urothelial cell carcinoma", BJU International, 101(7), (Apr. 2008), 894-901.

Mayer, R., et al., "A randomized controlled trial of intravesical bacillus calmette-guerin for treatment refractory interstitial cystitis", Journal of Urology, 173(4), (Apr. 2005), 1186-1191.

Miller, R L, et al., "Imiquimod applied topically: a novel immune response modifier and new class of drug", Int J Immunopharmacol., 21(1), (Jan. 1999), 1-14.

Mosmann, T. R., et al., "TH1 and TH2 cells: different patterns of lymphokine secretion lead to different functional properties", Annual Review Immunology, 7, (1989), 145-173.

Rohn, S., et al., "Antioxidant activity of protein-bound quercetin", J Agric Food Chem., 52(15), (Jul. 28, 2004), 4725-9.

Schon, M., et al., "Tumor-Selective Induction of Apoptosis and the Small-Molecule Immune Response Modifier Imiquimod", J Natl Cancer Inst, 95(15), (2003), 1138-1149.

Sidky, Y. A., et al., "Curative effectiveness of the interferon inducing imiquimod as a signal agent in mouse bladder tumors", Proceedings, Eighty-Fourth Meeting of the American Association for Cancer Research, vol. 34, (Abstract 2789) (May 19-22, 1993, Orlando, FL), (Mar. 1993), p. 467.

Sidky, Y. A, et al., "Effects of Treatment with an Oral Interferon Inducer, Imidazoquinolinamine (R-837), on the Growth of Mouse Bladder Carcinoma FCB", Journal of Interferon Research, 10(Supp 1), (Abstract II6-12) (Annual Meeting of the ISIR, San Francisco, CA, Nov. 14-18, 1990), (Nov. 1990), S123.

Sidky, Y. A., et al., "Effects of treatment with the oral interferon inducer, R-837, on the growth of mouse colon carcinoma, MC-26", Proceedings, 81st Annual Meeting of the American Association for Cancer Research, vol. 31, (Abstract 2574), (Mar. 1990), p. 433.

Sidky, Y. A, et al., "Inhibition of murine tumor growth by an interferon-inducing imidazoquinolinamine", Cancer Research, 52(13), (Jul. 1, 1992), 3528-33.

Sidky, Y. A., et al., "Inhibition of tumor-induced angiogenesis by the interferon inducer Imiquimod", Proceedings, Eighty-Third Annual Meeting of the American Association of Cancer Research, vol. 33, (Abstract 458) (May 20-23, 1992, San Diego, CA), (Mar. 1992), p. 77.

Simons, M. P., et al., "Identification of the Mycobacterial Subcomponents Involved in the Release of Tumor Necrosis Factor-Related Apoptosis-Inducing Ligand from Human Neutrophils", Infection and Immunity, 75(3), (2007), 1265-1271.

Smith, E. B., et al., "Antitumor Effects of Imidazoquinolines in Urothelial Cell Carcinoma of the Bladder", The Journal of Urology, 177(6), (Abstract Only), (2007), 1 pg.

Smith, E. B, et al., "Antitumor effects of imidazoquinolines in urothelial cell carcinoma of the bladder", J Urol., 177(6), (Jun. 2007), 2347-51.

Smith, E. B., et al., "Effects of Imiquimod, a toll-like receptor-7 agonist, on cell proliferation and cytokine production in bladder cancer in vitro and in vivo", Journal of Urology, 173(4, Suppl. S), (Apr. 2005), p. 158.

Veronese, F. M., et al., "The impact of PEGylation on biological therapies", BioDrugs, 22(5), (2008), 315-329.

Wille-Reece, U., et al., "HIV Gag protein conjugated to a Toll-like receptor 7/8 agonist improves the magnitude and quality of Th1 and CD8+ T cell responses in nonhuman primates", Proc. Natl. Acad. Sci. USA, 102(42), (Oct. 18, 2005), 15190-15194.

Wu, C., et al., "Immunotherapeutic activity of a conjugate of a Toll-like receptor 7 ligand", Proc. Natl. Acad. Sci. USA, 104(10), (2007), 3990-3995.

Zaks, K, et al., "Efficient immunization and cross-priming by vaccine adjuvants containing TLR3 or TLR9 agoinst complexed to cationic Liposomes", Journal of Immunology, 176(12), (Jun. 15, 2006), 7335-7345.

"U.S. Appl. No. 12/027,960, 312 Amendment filed Nov. 1, 2012", 7 pgs.

"U.S. Appl. No. 12/064,529, Preliminary Amendment filed Feb. 22, 2008", 11 pgs.

"U.S. Appl. No. 12/704,343, Advisory Action mailed Apr. 5, 2013", 3 pgs.

"U.S. Appl. No. 12/704,343, Examiner Interview Summary mailed Feb. 7, 2013", 3 pgs.

"U.S. Appl. No. 12/704,343, Examiner Interview Summary mailed Feb. 25, 2013", 3 pgs.

"U.S. Appl. No. 12/704,343, Final Office Action mailed May 10, 2013", 7 pgs.

"U.S. Appl. No. 12/704,343, Final Office Action mailed Dec. 7, 2012", 10 pgs.

"U.S. Appl. No. 12/704,343, Response filed Feb. 27, 2013 to Final Office Action mailed Dec. 7, 2012", 9 pgs.

"U.S. Appl. No. 13/682,208, Preliminary Amendment filed Nov. 20, 2012", 7 pgs.

"U.S. Appl. No. 13/682,208, Restriction Requirement mailed Jun. 6, 2013", 9 pgs.

"U.S. Appl. No. 13/736,545, Preliminary Amendment filed Mar. 6, 2013", 3 pgs.

"U.S. Appl. No. 13/791,175, Non Final Office Action mailed Jun. 7, 2013", 11 pgs.

"U.S. Appl. No. 13/791,175, Preliminary Amendment filed Mar. 8, 2013", 4 pgs.

"Aromatic Ions (Chemgapedia)", [Online] Retrieved From Internet: <http://www.chemgapedia.de/vsengine/vlu/vsc/en/ch/12/oc/vlu_organik/aromaten/aromaten/aromaten_gesamt.vlu/Page/vsc/en/ch/12/oc/aromaten/aromaten/ar_ionen/ar_ionen.vscml.html>, (Dec. 3, 2012).

"Chinese Application Serial. No. 200980112411.7—Translation of the cited CN OA", 8 pgs, (Nov. 5, 2012).

"Eurasian Application Serial No. 200901078—Pending Claims", 2 pgs, (Jan. 16, 2013).

"Japanese Patent Application Serial No. 2008-528017—Translation of Office Action", 4 pgs, Mailed May 22, 2012.

Butler, Roslyn S, et al., "Highly fluorescent donor-acceptor purines", J. Mater. Chem., 17, (2007), 1863-1865.

Metzler, David E, "Biosynthesis of triglycerides and phospholipids", Biochemistry: The Chemical Reactions of Living Cells, (1977), 708.

"U.S. Appl. No. 12/302,738, Response filed Dec. 3, 2013 to Final Office Action mailed Oct. 3, 2013", 8 pgs.

"U.S. Appl. No. 12/704,343, Notice of Allowance mailed Jan. 3, 2014", 11 pgs.

"U.S. Appl. No. 12/704,343, Notice of Allowance mailed Aug. 2, 2013", 10 pgs.

"U.S. Appl. No. 12/704,343, Response filed Jul. 10, 2013 to Final Office Action mailed May 10, 2013", 8 pgs.

"U.S. Appl. No. 13/682,208, Non Final Office Action mailed Nov. 7, 2013", 13 pgs.

"U.S. Appl. No. 13/682,208, Response filed Aug. 7, 2013 to Restriction Requirement mailed Jun. 6, 2013", 8 pgs.

"U.S. Appl. No. 13/736,545, Notice of Allowance mailed Aug. 2, 2013", 9 pgs.

"U.S. Appl. No. 13/791,175 , Response filed Nov. 1, 2013 to Non Final Office Action mailed Jun. 7, 2013", 8 pgs.

"U.S. Appl. No. 13/791,175, Final Office Action mailed Dec. 26, 2013", 12 pgs.

"European Application Serial No. 07755916.9, Examination Notification Art. 94(3) mailed Aug. 15, 2013", 4 pgs.

"International Application Serial No. PCT/US2007/009840, International Search Report mailed Aug. 5, 2008", 4 pgs.

"International Application Serial No. PCT/US2007/009840, Written Opinion mailed Aug. 5, 2008", 7 pgs.

Julien, R. M., "Chapter 2: Pharmacodynamics: How Drugs Act", A Primer of Drug Action (Ninth Edition); Worth Publishers, (2001), 37-57.

Lippard, Stephen J, et al., "Chemical synthesis: The art of chemistry", Nature, 416, (2002), p. 587.

U.S. Appl. No. 13/682,208, Response filed Feb. 7, 2014 to Non Final Office Action mailed Nov. 7, 2013, 9 pgs.

(56) References Cited

OTHER PUBLICATIONS

U.S. Appl. No. 13/736,545, Notice of Allowance mailed Mar. 18, 2014, 6 pgs.

European Application Serial No. 07755916.9, Office Action mailed Mar. 25, 2014, 1 pg.

European Application Serial No. 13001957.3, Extended European Search Report mailed Jan. 28, 2014, 17 pgs.

European Application Serial No. 13001957.3, Office Action mailed Mar. 3, 2014, 2 pgs.

Anders. H.-J., et al., "Molecular mechanisms of autoimmunity triggered by microbial infection", *Arthritis Research & Therapy*, 7(5), (2005), 215-224.

Staros, E. B., et al., "New Approaches to Understanding Its Clinical Significance", *Am. J. Clin. Pathol.*, 123(2), (2005), 305-312.

Takeda, K., et al., "Toll-like receptors in innate immunity". *International Immunology*, 17(1). (2005), 1-14.

U.S. Appl. No. 12/367,172, Non Final Office Action mailed Jul. 1, 2014, 20 pgs.

U.S. Appl. No. 13/682,208, Final Office Action mailed May 23, 2014, 17 pgs.

European Application Serial No. 07755916.9, Response filed May 23, 2014 to Examination Notification Art. 94(3) mailed Aug. 15, 2013, 13 pgs.

"Definition: Micelle", Merriam-Webster, [Online]. Retrieved from the Internet: <URL:http://www.merriam-webster.com/dictionary/micelle>, (Accessed on Jun. 25, 2014), 1 pg.

Brown, Gordon, "Dectin-1: a signalling non-TLR pattern-recognition receptor", Nature Reviews Immunology, (2006), 33-43.

Jacobson, Kenneth A, et al., "Adenosine analogs with covalently attached lipids have enhanced potency at Al-adenosine receptors", FEBS Letters, 225(1-2), (1987), 97-102.

Japanese Application Serial No. 2009-549102, Voluntary Amendment filed Feb. 7, 2011, 24 pgs.

U.S. Appl. No. 13/791,175, Non Final Office Action mailed Jul. 21, 2014, 11 pgs.

U.S. Appl. No. 13/791,175, Response filed Jun. 26, 2014 to Final Office Action mailed Dec. 26, 2013, 9 pgs.

\* cited by examiner

PURINE ANALOGS

CROSS-REFERENCE TO RELATED APPLICATIONS

This application is a U.S. national stage filing under 35 U.S.C. 371 from International Application No. PCT/US2007/009840 filed Apr. 23, 2007 and published in English as WO 2007/142755 A2/A3 on Dec. 13, 2007, claiming priority from U.S. provisional application Ser. No. 60/810,184 filed May 31, 2006; which applications and publication are incorporated herein by reference and made a part hereof.

GOVERNMENT FUNDING

The invention was made with government support under grant numbers AI56463 and AI57436 awarded by the National Institutes of Health. As a result, the U.S. government may have certain rights in this invention.

TECHNICAL FIELD OF THE INVENTION

This invention concerns compounds having utility in the treatment of disease in animals, particularly in humans. Specifically, it concerns compositions of novel purine analogs, and methods of using such compounds to effect desired prophylactic and/or therapeutic outcomes.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

Discovering treatments for the many diseases that afflict humans and other organisms is a major focus of modern science. Among these diseases are cancer, infectious disease, and autoimmune disease. While much has been learned about the mechanisms of these and other diseases, and while a number of treatments have been developed, the need for additional, and in many instances, improved, treatments, is desired.

Taking cancer as an example, it is now the second leading cause of death in the United States, and over 8,000,000 persons in the United States have been diagnosed with cancer. In 1995, cancer accounted for 23.3% of all deaths in the United States. See U.S. Dept. of Health and Human Services, National Center for Health Statistics, Health United States 1996-97 and Injury Chartbook 117 (1997).

Cancer is not fully understood on the molecular level. It is known that exposure of a cell to a carcinogen such as certain viruses, certain chemicals, or radiation, leads to DNA alteration that inactivates a "suppressive" gene or activates an "oncogene". Suppressive genes are growth regulatory genes, which upon mutation, can no longer control cell growth. Oncogenes are initially normal genes (called proto-oncogenes) that by mutation or altered context of expression become transforming genes. The products of transforming genes cause inappropriate cell growth. More than twenty different normal cellular genes have been discovered to become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

A neoplasm, or tumor, is an abnormal, unregulated, and disorganized proliferation of cell growth, and is generally referred to as cancer. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Cancer is now primarily treated with one or a combination of three types of therapies: surgery; radiation; and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer.

The adverse effects of systemic chemotherapy used in the treatment of neoplastic disease are most feared by patients undergoing treatment for cancer. Of these adverse effects, nausea and vomiting are the most common. Other adverse side effects include cytopenia, infection, cachexia, mucositis in patients receiving high doses of chemotherapy with bone marrow rescue or radiation therapy; alopecia (hair loss); cutaneous complications such as pruritis, urticaria, and angioedema; neurological complications; pulmonary and cardiac complications; and reproductive and endocrine complications. Drug-induced side effects significantly impact the quality of life of the patient and may dramatically influence patient compliance with treatment.

Given the number of different cancers that are known, differences in patient response and tolerance to different treatments, and the side effects that frequently accompany chemotherapy, it is clear that new compounds and improved methods of treatment are needed.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

An "agent" refers to an active ingredient delivered to achieve an intended therapeutic benefit.

The term "combination therapy" refers to a therapeutic regimen that involves the provision of at least two distinct therapies to achieve an indicated therapeutic effect. For example, a combination therapy may involve the administration of two or more chemically distinct active ingredients, or agents, for example, a TLR agonist and calcitonin. Alternatively, a combination therapy may involve the administration of one or more TLR agonists, alone or in conjunction with another agent as well as the delivery of another therapy. In the context of the administration of two or more chemically distinct agents, it is understood that the active ingredients may be administered as part of the same composition or as different compositions. When administered as separate compositions, the compositions comprising the different active ingredients may be administered at the same or different times, by the same or different routes, using the same or different dosing regimens, all as the particular context requires and as determined by the attending physician. Similarly, when one or more agents are combined with, for example, psychoanalysis, the drug(s) may be delivered before, during, and/or after the period the subject is in therapy.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, such solids include dried compositions prepared by lyophilization, freeze-drying, precipitation, and similar procedures.

"Monotherapy" refers to a treatment regimen based on the delivery of one therapeutically effective compound, whether administered as a single dose or several doses over time.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

A "purine analog" refers to a synthetic (i.e., non-naturally occurring) molecule derived from a purine. The term "derivative" refers to metabolites of a compound of the invention that may result following administration of the compound, as well as to prodrug forms of a compound of the invention.

The term "species," when used in the context of describing a particular drug species, refers to a population of chemically indistinct molecules.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

SUMMARY OF THE INVENTION

It is an object of this invention to provide a novel class of patentable compounds having therapeutic utility. In general, these compounds are defined by Formula I, below, as well as conjugates that include such compounds:

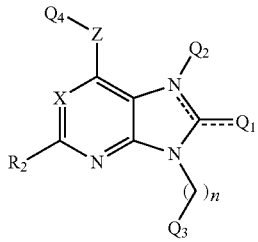

Formula I wherein:
X is a moiety selected from the group consisting of nitrogen and $CR_8$, wherein $R_8$ is a moiety selected from the group consisting of hydrogen, a halogen, a substituted or unsubstituted alkyl, and a substituted or unsubstituted heteroalkyl;

( - - - - ) is an optional double bond; wherein:
when $N = C$ is a double bond, $Q_2$ is not present;
when $C = Q_1$ is a double bond, $Q_1$ is a moiety selected from the group consisting of O, S, $NY_1$, and $NNY_2Y_3$; and
when $C = Q_1$ is a single bond, $Q_1$ is a moiety selected from the group consisting of hydrogen, $O-Y_2$, $S-Y_2$, $NY_1Y_2$, and $NY_2NY_3Y_4$, wherein
$Y_1$ is a moiety selected from the group consisting of hydrogen, a substituted or unsubstituted alkyl, a substituted or unsubstituted heteroalkyl, a substituted or unsubstituted aryl; a substituted or unsubstituted heteroaryl, a CO-substituted or unsubstituted alkyl, a COO-substituted or unsubstituted alkyl, cyano, nitro, hydroxyl, and $O-Y_2$; and
$Y_2$, $Y_3$, and $Y_4$ are each independently selected from the group consisting of hydrogen, a substituted or unsubstituted alkyl, a substituted or unsubstituted heteroalkyl, a substituted or unsubstituted aryl, and a substituted or unsubstituted heteroaryl, provided that when $Q_1$ is $O-Y_2$, $Y_2$ is not hydrogen;

Z is a moiety selected from the group consisting of oxygen, sulfur, and $NY_5$, wherein $Y_5$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$Q_2$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$Q_3$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$Q_4$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$R_2$ is a moiety selected from the group consisting of hydrogen, a substituted or unsubstituted alkyl, a substituted or unsubstituted heteroalkyl, $OY_6$, $SY_6$, and $NY_6Y_7$, wherein $Y_6$ and $Y_7$ are each independently selected from the group consisting of hydrogen, a substituted or unsubstituted alkyl, a substituted or unsubstituted heteroalkyl, a substituted or unsubstituted aryl, and a substituted or unsubstituted heteroaryl; and n is 0, 1, 2, 3 or 4;
or an isomer, metabolite, polymorph, prodrug, or salt thereof.

Thus, one aspect of the invention relates to compounds themselves, although when these compounds are not conjugated to another molecule, this class of compounds excludes those compounds represented by Formula (1x):

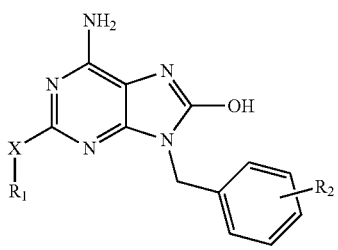

Formula 1x wherein:
- X is a moiety selected from the group consisting of sulfur, oxygen, and or NR³, wherein R³ is a moiety selected from the group consisting of hydrogen, a substituted or unsubstituted alkyl, and a substituted or unsubstituted heterocycle together with R¹ via the nitrogen of NR³;
- R¹ is a moiety selected from the group consisting of a substituted or unsubstituted alkyl, a substituted or unsubstituted aryl, and a substituted or unsubstituted heterocycle; and
- R² is one or more substituents of the benzene ring, wherein each substituent is independently selected from the group consisting of hydrogen, hydroxy, a substituted or unsubstituted lower alkl, a substituted or unsubstituted lower alkoxy, a substituted or unsubstituted lower alkanoyl, a substituted or unsubstituted aroyl, a carboxyl, a substituted or unsubstituted lower alkoxycarbonyl, an amino, a lower alkylamino, a di(lower alkyl) amino, a carbamoyl, a lower alkylcarbamoyl, a (lower alkyl) carbamoyl, cyano, a halogen, and nitro.

Preferred embodiments of the compounds of the invention include those represented by Formula II:

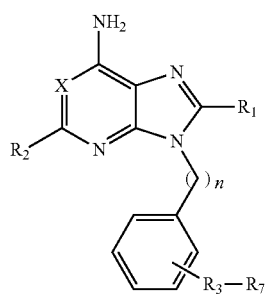

Formula II wherein:
- X is a moiety selected from the group consisting of nitrogen and $CR_8$, wherein $R_8$ is a moiety selected from the group consisting of hydrogen, a halogen, a substituted or unsubstituted alkyl, and a substituted or unsubstituted heteroalkyl;
- $R_1$ is a moiety selected from the group consisting of a nitro, cyano, hydroxylamino, alkoxylamino, hydrazino, substituted hydrazino, $NR_9R_{10}$, $NCOR_{11}$, and $NCOOR_{11}$, wherein $R_9$ and $R_{10}$ are each independently selected from the group consisting of hydrogen, $C_{1-8}$alkyl, $C_{3-6}$cycloalkyl, $C_{1-6}$alkyloxy$C_{1-6}$alkyl, $C_{1-6}$carbonyloxy$C_{1-6}$alkyl, mono- or di($C_{1-6}$alkyl)amino$C_{1-6}$alkyl, mono- or di(hydroxy$C_{1-6}$alkyl)amino$C_{1-6}$alkyl, aryl $C_{1-6}$alkyl, and heteroaryl$C_{1-6}$alkyl, each optionally substituted with 1 or 2 substituents each independently selected from the group consisting of $C_{3-6}$cycloalkyl, hydroxyl, $C_{3-4}$heteroaryl, $C_{3-6}$aryl, $C_{3-6}$heterocloalkyl, and $R_9$ and $R_{10}$ which, when taken together with the nitrogen atom to which they are attached, form an optionally substituted pyrrolidinyl, piperidinyl, homopiperidinyl, morpholino, or thiomorpholino group, wherein $R_{11}$ is $C_{1-6}$ alkyl and substituted alkyl; and
- $R_2$ is a moiety selected from the group consisting of $OR_{12}$, $SR_{12}$, $NR_{12}R_{13}$ wherein $R_{12}$ and $R_{13}$ is each a moiety independently selected from the group consisting of hydrogen, a substituted or unsubstituted alkyl, a substituted or unsubstituted heteroalkyl, a substituted or unsubstituted aryl, and a substituted or unsubstituted heteroaryl;
- $R_3$-$R_7$ is each a moiety independently selected from the group consisting of hydrogen, halogen, cyano, nitro, substituted or unsubstituted alkyl, substituted or unsubstituted heteroalkyl, $OR_{12}$, $SR_{12}$, $NR_{12}R_{13}$ or $COYR_{14}$, wherein $R_{12}$ and $R_{13}$ is each a moiety independently selected from the group consisting of hydrogen, a substituted or unsubstituted alkyl, a substituted or unsubstituted heteroalkyl, a substituted or unsubstituted aryl, and a substituted or unsubstituted heteroaryl, $R_{14}$ is a moiety selected from the group consisting of hydrogen, a substituted or unsubstituted alkyl, a substituted or unsubstituted heteroalkyl, and a substituted or unsubstituted heteroaryl, and Y selected from the group consisting of a bond, NH, and O; and
- n is 0, 1, 2, 3 or 4;

or an isomer, metabolite, polymorph, prodrug, or salt thereof.

Other preferred compounds include those represented by Formula III:

Formula III wherein:
- $R_1$ is a moiety selected from the group consisting of a nitro, cyano, hydroxylamino, alkoxylamino, hydrazino, substituted hydrazino, $NR_9R_{10}$, $NCOR_{11}$, and $NCOOR_{11}$, wherein $R_9$ and $R_{10}$ are each independently selected from the group consisting of hydrogen, $C_{1-8}$alkyl, $C_{3-6}$cycloalkyl, $C_{1-6}$alkyloxy$C_{1-6}$alkyl, $C_{1-6}$-carbonyloxy$C_{1-6}$alkyl, mono- or di($C_{1-6}$alkyl)amino$C_{1-6}$alkyl, mono- or di(hydroxy$C_{1-6}$alkyl)amino$C_{1-6}$alkyl, aryl $C_{1-6}$alkyl, and heteroaryl$C_{1-6}$alkyl, each optionally substituted with 1 or 2 substituents each independently selected from the group consisting of $C_{3-6}$cycloalkyl, hydroxyl, $C_{3-6}$heteroaryl, $C_{3-6}$aryl, $C_{3-6}$heterocycloalkyl, and $R_9$ and $R_{10}$ which, when taken together with the nitrogen atom to which they are attached, form an optionally substituted pyrrolidinyl, piperidinyl, homopiperidinyl, morpholino, or thiomorpholino group, wherein $R_{11}$ is a moiety selected from the group consisting of $C_{1-6}$ alkyl and substituted alkyl; and $R_2$ is a moiety selected from the group consisting of $OR_{12}$, $SR_{12}$, $NR_{12}R_{13}$ wherein $R_{12}$ and $R_{13}$ is each a moiety independently selected from the group consisting of hydrogen, a substituted or unsubstituted alkyl, a substituted or unsubstituted heteroalkyl, a substituted or unsubstituted aryl, and a substituted or unsubstituted heteroaryl; and $R_3$ is a moiety selected from the group consisting of hydrogen, a substituted or unsubstituted alkyl, a substituted or unsubstituted heteroalkyl, a substituted or unsubstituted aryl, a substituted or unsubstituted heteroaryl, $(CH_2)_nNR_4R_5$, $(CH_2)_nCONR_4R_5$, $(CH_2)_nNCONR_4R_5$, and $(CH_2)_nNCSNR_4R_5$, wherein $R_4$ and $R_5$ are each independently selected from the group consisting of hydrogen, $C_{1-8}$alkyl, $C_{3-6}$cycloalkyl, $C_{1-6}$alkyloxy $C_{1-6}$alkyl, $C_{1-6}$-carbonyloxy$C_{1-6}$alkyl, $C_{1-6}$-carbonyloxy$C_{1-6}$alkyl, mono- or di($C_{1-6}$alkyl)amino$C_{1-6}$alkyl, mono- or di(hydroxy$C_{1-6}$alkyl)amino, $C_{1-6}$ alkyl, aryl$C_{1-6}$alkyl, and heteroaryl$C_{1-6}$alkyl, each optionally substituted with 1 or 2 substituents each independently selected from the group consisting of halogen, hydroxyl, $C_{3-6}$cycloalkyl, $C_{3-6}$heterocycloalkyl, $C_{3-6}$heteroaryl, and $C_{3-6}$aryl; and n is 0, 1, 2, 3 or 4;

or an isomer, metabolite, polymorph, prodrug, or salt thereof.

The invention also includes conjugates of these compounds, as represented by any of Formulas I-III, conjugated to another chemical entity.

A related aspect of the invention concerns compositions, which comprise a compound of the invention in combination with a carrier. Such compositions can be in liquid or dry form. In the context of therapy, such compositions preferably are pharmaceutically acceptable formulations.

Another related aspect of the invention addresses methods of synthesizing the instant compounds and compositions.

Yet another aspect of the invention relates to methods of administering the compositions of the invention.

Another related aspect concerns methods of using compounds and compositions of the invention, for example, to prevent and/or treat disease, including cancer and infections, in humans and other animals.

These and other aspects of the invention are described below.

BRIEF DESCRIPTION OF THE FIGURES

There are no figures in this application.

As those in the art will appreciate, the following description describes certain preferred embodiments of the invention in detail, and is thus only representative and does not depict the actual scope of the invention. Before describing the present invention in detail, it is understood that the invention is not limited to the particular molecules, systems, and methodologies described, as these may vary. It is also to be understood that the terminology used herein is for the purpose of describing particular embodiments only, and is not intended to limit the scope of the invention defined by the appended claims.

DETAILED DESCRIPTION OF THE INVENTION

The present invention is based on the invention of a patentable new class of purine analog compounds, namely those represented by formula (I):

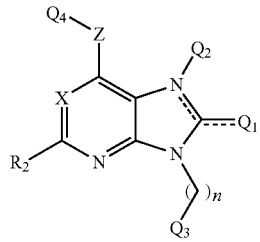

Formula I wherein:

X is a moiety selected from the group consisting of nitrogen and $CR_8$, wherein $R_8$ is a moiety selected from the group consisting of hydrogen, a halogen, a substituted or unsubstituted alkyl, and a substituted or unsubstituted heteroalkyl;

( ----- ) is an optional double bond; wherein:

when $N = C$ is a double bond, $Q_2$ is not present;

when $C = Q_1$ is a double bond, $Q_1$ is a moiety selected from the group consisting of O, S, $NY_1$, and $NNY_2Y_3$; and when $C = Q_1$ is a single bond, $Q_1$ is a moiety selected from the group consisting of hydrogen, O—$Y_2$, S—$Y_2$, $NY_1Y_2$, and $NY_2NY_3Y_4$, wherein $Y_1$ is a moiety selected from the group consisting of hydrogen, a substituted or unsubstituted alkyl, a substituted or unsubstituted heteroalkyl, a substituted or unsubstituted aryl; a substituted or unsubstituted heteroaryl, a CO-substituted or unsubstituted alkyl, a COO-substituted or unsubstituted alkyl, cyano, nitro, hydroxyl, and O—$Y_2$; and $Y_2$, $Y_3$, and $Y_4$ are each independently selected from the group consisting of hydrogen, a substituted or unsubstituted alkyl, a substituted or unsubstituted heteroalkyl, a substituted or unsubstituted aryl, and a substituted or unsubstituted heteroaryl, provided that when $Q_1$ is O—$Y_2$, $Y_2$ is not hydrogen;

Z is a moiety selected from the group consisting of oxygen, sulfur, and $NY_5$, wherein $Y_5$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$Q_2$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$Q_3$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$Q_4$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;

$R_2$ is a moiety selected from the group consisting of hydrogen, a substituted or unsubstituted alkyl, a substituted or unsubstituted heteroalkyl, $OY_6$, $SY_6$, and $NY_6Y_7$, wherein $Y_6$ and $Y_7$ are each independently selected from the group consisting of hydrogen, a substituted or unsubstituted alkyl, a substituted or unsubstituted heteroalkyl, a substituted or unsubstituted aryl, and a substituted or unsubstituted heteroaryl; and n is 0, 1, 2, 3 or 4;

or an isomer, metabolite, polymorph, prodrug, or salt thereof, but excluding

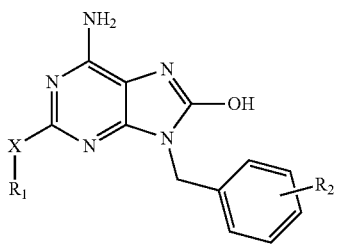

Formula 1x wherein:
- X is a moiety selected from the group consisting of sulfur, oxygen, and or $NR^3$, wherein $R^3$ is a moiety selected from the group consisting of hydrogen, a substituted or unsubstituted alkyl, and a substituted or unsubstituted heterocycle together with $R^1$ via the nitrogen of $NR^3$;
- $R^1$ is a moiety selected from the group consisting of a substituted or unsubstituted alkyl, a substituted or unsubstituted aryl, and a substituted or unsubstituted heterocycle; and
- $R^2$ is one or more substituents of the benzene ring, wherein each substituent is independently selected from the group consisting of hydrogen, hydroxy, a substituted or unsubstituted lower alkl, a substituted or unsubstituted lower alkoxy, a substituted or unsubstituted lower alkanoyl, a substituted or unsubstituted aroyl, a carboxyl, a substituted or unsubstituted lower alkoxycarbonyl, an amino, a lower alkylamino, a di(lower alkyl) amino, a carbamoyl, a lower alkylcarbamoyl, a (lower alkyl) carbamoyl, cyano, a halogen, and nitro.

While not wishing to be bound by a particular theory, it is believed that the compounds of the invention have dual functions. Initially, they are believed to stimulate components of the innate immune system, followed then by exertion of cytotoxic effects. Briefly, much has been learned recently about the molecular basis of innate recognition of microbial pathogens. Now it is generally accepted that many somatic cells express a range of receptors that detect potential pathogens independently of the adaptive immune system. These receptors are believed to interact with microbial components termed pathogen associated molecular patterns (PAMPs). Examples of PAMPs include peptidoglycans, lipotechoic acids from gram-positive cell walls, the sugar mannose (which is common in microbial carbohydrates but rare in humans), bacterial DNA, double-stranded RNA from viruses, and glucans from fungal cell walls. PAMPs generally meet certain criteria, including (a) expression by microbes but not in their mammalian hosts, (b) structural conservation across the wide range of pathogens, and (c) a capacity to stimulate innate immunity.

Toll-like Receptors (TLRs) have been found to play a central role in the detection of PAMPs and in the early response to microbial infections. See Underhill, et al. (2002), Curr Opin Immunol, vol. 14:103-110. At least ten mammalian TLR species and a number of naturally occurring and synthetic agonists have been identified. For example, TLR7 and TLR9 recognize and respond to imiquimod and immunostimulatory CpG oligonucleotides (ISS-ODN), respectively. The synthetic immunomodulator R-848 (resiquimod) activates both TLR7 and TLR8. While TLR stimulation initiates a common signaling cascade (involving the adaptor protein MyD88, the transcription factor NF-kB, and pro-inflammatory and effector cytokines), certain cell types tend to produce certain TLRs. For example, TLR7 and TLR9 are found predominantly on the internal faces of endosomes in dendritic cells (DCs) and B lymphocytes in humans. TLR8, on the other hand, is found predominantly in human blood monocytes.

Interferons (INFs) are also involved in the efficient induction of an immune response, especially after viral infection. However, many viruses produce proteins that block interferon production or action at various levels. Antagonism of interferon is believed to be part of a general strategy employed by pathogens to evade innate, as well as adaptive, immunity. While TLR agonists alone may be sufficiently active for some methods of treatment, in some instances the microbial interferon antagonists could mitigate the adjuvant effects of synthetic TLR agonists. Thus, the capacity to stimulate innate immunity, particularly the expression of pro-inflammatory and effector cytokines, would be particularly useful, and is an activity possessed by those compounds of the invention intended for therapeutic application. Indeed, when conjugated to macromolecules or even whole cells, the compounds of the invention will be even more potent stimulators of the immune system.

1. Compounds

The compounds of the invention are broad-spectrum, long-lasting, non-toxic synthetic immunostimulatory agents useful for activating the immune system of a mammal, particularly a human. Such compounds include a pharmacophore that is a purine analog that is a TLR agonist, i.e., a compound that stimulates signalling activity of a TLR receptor, particularly a TLR7, TLR8, or TLR9 receptor. Thus, a TLR7 agonist is one that stimulates TLR7 signalling activity preferentially as compared to the signalling activities of other TLR species, a TLR8 agonist is one that stimulates TLR8 signalling activity preferentially as compared to the signalling activities of other TLR species, and a TLR9 agonist is one that stimulates TLR9 signalling activity preferentially as compared to the signalling activities of other TLR species. The ability of a compound of the invention to act as a TLR agonist may be determined using any suitable technique, including pharmacological models which are well known to the art. See, e.g., Lee et al., PNAS (2003), vol. 100: 6646-6651. In some embodiments, the compounds of the invention also include a macromolecule, or even a whole cell, conjugated to a purine analog of the invention.

As used herein, unless otherwise indicated a "purine analog" refers generally to a patentable TLR agonist compound represented by formula (I), or an isomer, metabolite, polymorph, or prodrug, or a pharmaceutically acceptable salt of any such compound:

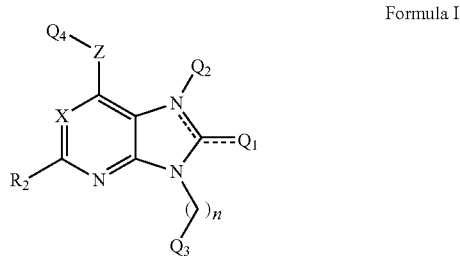

Formula I wherein:
- X is a moiety selected from the group consisting of nitrogen and $CR_8$, wherein $R_8$ is a moiety selected from the group consisting of hydrogen, a halogen, a substituted or unsubstituted alkyl, and a substituted or unsubstituted heteroalkyl;

(----) is an optional double bond; wherein:
  when N═C is a double bond, $Q_2$ is not present;
  when C═$Q_1$ is a double bond, $Q_1$ is a moiety selected from the group consisting of O, S, $NY_1$, and $NNY_2Y_3$; and
  when C═$Q_1$ is a single bond, $Q_1$ is a moiety selected from the group consisting of hydrogen, O—$Y_2$, S—$Y_2$, $NY_1Y_2$, and $NY_2NY_3Y_4$, wherein
    $Y_1$ is a moiety selected from the group consisting of hydrogen, a substituted or unsubstituted alkyl, a substituted or unsubstituted heteroalkyl, a substituted or unsubstituted aryl; a substituted or unsubstituted heteroaryl, a CO-substituted or unsubstituted alkyl, a COO-substituted or unsubstituted alkyl, cyano, nitro, hydroxyl, and O—$Y_2$; and
    $Y_2$, $Y_3$, and $Y_4$ are each independently selected from the group consisting of hydrogen, a substituted or unsubstituted alkyl, a substituted or unsubstituted heteroalkyl, a substituted or unsubstituted aryl, and a substituted or unsubstituted heteroaryl, provided that when $Q_1$ is O—$Y_2$, $Y_2$ is not hydrogen;
  Z is a moiety selected from the group consisting of oxygen, sulfur, and $NY_5$, wherein $Y_5$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;
  $Q_2$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;
  $Q_3$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;
  $Q_4$ is a moiety selected from the group consisting of hydrogen, a substituted or unsubstituted alkyl, a substituted or unsubstituted heteroalkyl, a substituted or unsubstituted aryl, and a substituted or unsubstituted heteroaryl;
  $R_2$ is a moiety selected from the group consisting of hydrogen, a substituted or unsubstituted alkyl, a substituted or unsubstituted heteroalkyl, $OY_6$, $SY_6$, and $NY_6Y_7$, wherein $Y_6$ and $Y_7$ are each independently selected from the group consisting of hydrogen, a substituted or unsubstituted alkyl, a substituted or unsubstituted heteroalkyl, a substituted or unsubstituted aryl, and a substituted or unsubstituted heteroaryl; and
  n is 0, 1, 2, 3 or 4;
or an isomer, metabolite, polymorph, prodrug, or salt thereof, but excluding

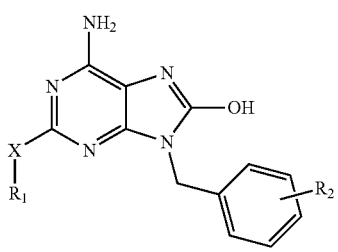

Formula 1x wherein:
  X is a moiety selected from the group consisting of sulfur, oxygen, and or $NR^3$, wherein $R^3$ is a moiety selected from the group consisting of hydrogen, a substituted or unsubstituted alkyl, and a substituted or unsubstituted heterocycle together with $R^1$ via the nitrogen of $NR^3$;
  $R^1$ is a moiety selected from the group consisting of a substituted or unsubstituted alkyl, a substituted or unsubstituted aryl, and a substituted or unsubstituted heterocycle; and
  $R^2$ is one or more substituents of the benzene ring, wherein each substituent is independently selected from the group consisting of hydrogen, hydroxy, a substituted or unsubstituted lower alkl, a substituted or unsubstituted lower alkoxy, a substituted or unsubstituted lower alkanoyl, a substituted or unsubstituted aroyl, a carboxyl, a substituted or unsubstituted lower alkoxycarbonyl, an amino, a lower alkylamino, a di(lower alkyl) amino, a carbamoyl, a lower alkylcarbamoyl, a (lower alkyl) carbamoyl, cyano, a halogen, and nitro.

The term "alkenyl" refers to an unsubstituted or substituted hydrocarbon chain radical having from 2 to about 15 carbon atoms, preferably from 2 to about 10 carbon atoms, more preferably from 2 to about 8 carbon atoms, and most preferably from about 2 to about 6 carbon atoms. Alkenyls have at least one olefinic double bond. Non-limiting examples of alkenyls include vinyl, allyl, and butenyl.

The term "alkoxy" or "alkyloxy" refers to an oxygen radical having an alkyl, alkenyl, or alkynyl, preferably an alkyl or alkenyl, and most preferably an alkyl, substituent. Examples of alkoxy radicals include —O-alkyl and —O-alkenyl. An alkoxy radical may be substituted or unsubstituted.

The term "alkoxyamino" used herein, alone or in combination with other radicals, denotes an alkoxy group attached to an amino group.

The term "aryloxy" refers to an oxygen radical having an aryl substituent. An aryloxy radical may be substituted or unsubstituted.

The term "alkyl" refers to an unsubstituted or substituted saturated hydrocarbon chain radical having from 1 to about 15 carbon atoms, preferably from 1 to about 10 carbon atoms, more preferably from 1 to about 6 carbon atoms, and most preferably from 1 to about 4 carbon atoms. Preferred alkyls include, for example, methyl, ethyl, propyl, iso-propyl, and butyl.

The term "alkylene" refers to an alkyl, alkenyl, or alkynyl that is a diradical. For example, "methylene" is —$CH_2$—. Alkylenes may be substituted or unsubstituted.

The term "alkynyl" refers to an unsubstituted or substituted hydrocarbon chain radical having from 2 to about 15 carbon atoms, preferably from 2 to about 10 carbon atoms, more preferably from 2 to about 8 carbon atoms, and most preferably from about 2 to about 6 carbon atoms. Alkynyls have at least one triple bond.

The term "aryl" refers to an aromatic ring radical that is either carbocyclic or heterocyclic. Preferred aryl groups include, for example, phenyl, benzyl, tolyl, xylyl, cumenyl, napthyl, biphenyl, thienyl, furyl, pyrrolyl, pyridinyl, pyrazinyl, thiazolyl, pyrimidinyl, quinolinyl, triazolyl, tetrazolyl, benzothiazolyl, benzofuryl, indolyl, indenyl, azulenyl, fluorenyl, anthracenyl, oxazolyl, isoxazolyl, isotriazolyl, imidazolyl, pyraxolyl, oxadiazolyl, indolizinyl, indolyl, isoindolyl, purinyl, quinolizinyl, quinolinyl, isoquinolinyl, cinnolinyl, and the like. Aryls may be substituted or unsubstituted.

The term "arylalkenyl" is an alkenyl radical substituted with an aryl group or an aryl radical substituted with an alkenyl group. Arylalkenyls may be substituted or unsubstituted.

The term "arylalkyl" is an alkyl radical substituted with an aryl group or an aryl radical substituted with an alkyl group.

Preferred arylalkyl groups include benzyl, phenylethyl, and phenylpropyl. Arylalkyls may be substituted or unsubstituted.

The term "biohydrolyzable amide" refers to an amide of a compound that does not interfere with the activity of the compound, or that is readily converted in vivo by a mammalian subject to yield an active compound. A "biohydrolyzable ester" is an ester that does not interfere with the activity of the compound, or that is readily converted in vivo by a mammalian subject to yield an active compound. A "biohydrolyzable imide" is an imide that does not interfere with the activity of the compound, or that is readily converted in vivo by a mammalian subject to yield an active compound.

The term "carbocyclic ring", "carbocycle", and the like refer to a hydrocarbon ring radical. Carbocyclic rings are monocyclic or are fused, bridged, or spiro polycyclic rings. Unless otherwise specified, monocyclic rings contain from 3 to about 9 atoms, preferably from about 4 to about 7 atoms, and most preferably 5 or 6 atoms. Polycyclic rings contain from about 7 to about 17 atoms, preferably from about 7 to about 14 atoms, and most preferably 9 or 10 atoms. Carbocyclic rings (carbocycles) may be substituted or unsubstituted.

The term "cycloalkyl" refers to a saturated carbocyclic or heterocyclic ring radical. Preferred cycloalkyl groups include, for example, cyclobutyl, cyclopentyl, and cyclohexyl. Cycloalkyls may be substituted or unsubstituted.

The term "cycloalkenyl" refers to an unsaturated carbocyclic or heterocyclic ring radical having at least one double bond. Cycloalkenyls may be substituted or unsubstituted.

The term "halogen" (or "halos" or the like) refers to bromine, chlorine, iodine, and fluorine, more preferably, bromine, chlorine, and iodine, even more preferably bromine and chlorine, and most preferably chlorine.

The term "heteroalkenyl" refers to an alkenyl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkenyls may be substituted or unsubstituted.

The term "heteroalkyl" refers to an alkyl radical comprised of carbon atoms and one or more heteroatoms wherein the heteroatoms are selected from the croup consisting of oxygen, sulfur, nitrogen, and phosphorous, more preferably, oxygen, sulfur, and nitrogen. Heteroalkyls may be substituted or unsubstituted.

The term "heteroalkynyl" refers to an alkynyl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkynyls may be substituted or unsubstituted.

The term "heteroaryl" refers to an aryl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroaryls may be substituted or unsubstituted.

The term "heteroarylalkenyl" refers to an arylalkenyl radical wherein the aryl group and/or the alkenyl group is comprised of carbon atoms and one or more heteroatoms wherein the heteroatoms are selected from the group consisting of oxygen, sulfur, nitrogen, and phosphorous, more preferably, oxygen, sulfur, and nitrogen. Heteroarylalkenyls may be substituted or unsubstituted.

The term "heterocyclic ring", "heterocycle", and the like refers to a ring radical comprised of carbon atoms and one or more heteroatoms in the ring, wherein the heteroatoms are selected from the group consisting of oxygen, sulfur, nitrogen, and phosphorous, more preferably, oxygen, sulfur, and nitrogen. Heterocycles are monocyclic or are fused, bridged, or spiro polycyclic rings. Unless otherwise specified, monocycles contain from 3 to about 9 atoms, preferably from about 4 to about 7 atoms, and most preferably 5 or 6 atoms. Polycycles contain from about 7 to about 17 atoms, preferably from about 7 to about 14 atoms, and most preferably 9 or 10 atoms. Heterocyclic rings (heterocycles) may be substituted or unsubstituted.

The term "heterocycloalkyl" refers to a cycloalkyl having at least one heteroatom in the ring. Heterocycloalkyls may be substituted or unsubstituted.

The term "heterocycloalkenyl" refers to a cycloalkenyl having at least one heteroatom in the ring. Heterocycloalkyls may be substituted or unsubstituted.

The term "hydrazino", either alone or in combination with other radicals, denotes —NHNH—, and may be substituted or unsubstituted.

The term "hydroxylamino" used herein, alone or in combination with other radicals, denotes an —NHOH moiety, and may be substituted or unsubstituted.

A "lower" moiety (e.g., "lower" alkyl) is moiety having 1 to about 6, preferably 1 to about 4, carbon atoms. Specifically, lower alkyl refers to ($C_1$-$C_6$)alkyl and includes methyl, ethyl, propyl, isopropyl, butyl, iso-butyl, sec-butyl, pentyl, 3-pentyl, or hexyl; ($C_3$-$C_6$)cycloalkyl includes cyclopropyl, cyclobutyl, cyclopentyl, or cyclohexyl; lower alkoxy refers to ($C_1$-$C_6$)alkoxy and includes methoxy, ethoxy, propoxy, isopropoxy, butoxy, iso-butoxy, sec-butoxy, pentoxy, 3-pentoxy, or hexyloxy; lower alkenyl refers to ($C_1$-$C_6$)alkenyl and includes vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; lower alkynyl refers to ($C_1$-$C_6$)alkynyl and includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; (hydroxy)lower alkyl refers to (hydroxy)($C_1$-$C_6$)alkyl and includes hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; lower alkanoyloxy refers to ($C_2$-$C_6$)alkanoyloxy and includes acetoxy, propanoyloxy, butanoyloxy, isobutanoyloxy, pentanoyloxy, or hexanoyloxy.

As used herein unless otherwise specified, the term "substituted" in reference to a group, moiety, and the like refers to one having one or more substituent groups each independently selected from hydrogen, alkyl, alkenyl, alkoxy, hydroxy, nitro, amino, alkylamino, cyano, halogen, thiol, aryl, cycloalkyl, heteroaryl, heterocycloalkyl (e.g., piperidinyl, morpholino, pyrrolidinyl), imino, hydroxyalkyl, aryloxy, and arylalkyl, preferably hydrogen, alkyl, alkenyl, alkoxy, hydroxy, nitro, amino, alkylamino, halo, thiol, and aryloxy, more preferably hydrogen, alkyl, alkenyl, alkoxy, hydroxy, nitro, amino, alkylamino, and halogen, even more preferably hydrogen, alkyl, and alkoxy, and most preferably alkoxy.

The compounds of the invention are preferably prepared as salts. The term "salt" refers to a cationic salt formed at any acidic (e.g., carboxyl) group, or an anionic salt formed at any basic (e.g., amino) group. Many salts are known in the art. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). When intended for administration to a subject, such salts should be appropriate for such use. Thus, the term "pharmaceutically acceptable" means suitable for use in humans, whereas "veterinarily acceptable" means suitable for use in non-human animals, particularly non-human mammals.

The term "pharmaceutically acceptable salt" refers to salts which retain the biological effectiveness and properties of the compounds of the invention and which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts, see, e.g., Berge, et al. ((1977) J. Pharm. Sci., vol. 66, 1).

The expression "non-toxic pharmaceutically acceptable salts" non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, fumaric, methanesulfonic, trifluoromethanesulfonic, and toluenesulfonic acid and the like. Salts also include those from inorganic bases, such as ammonia, sodium hydroxide, potassium hydroxide, and hydrazine. Suitable organic bases include methylamine, ethylamine, propylamine, dimethylamine, diethylamine, diethanolamine, trimethylamine, triethylamine, triethanolamine, ethylenediamine, hydroxyethylamine, morpholine, piperazine, and guanidine.

As those in the art will appreciate, where any variable, moiety, group, or the like occurs more than one time in any variable or structure, its definition at each occurrence is independent of its definition at every other occurrence. All percentages, ratios, and proportions used herein are by weight unless otherwise specified. Specific and preferred values listed below for radicals, substituents, and ranges, are for illustration only, and they do not exclude other defined values or other values within defined ranges for the radicals and substituents. The compounds of the invention are patentable compounds of formula I having any combination of the values, specific values, more specific values, and preferred values described herein.

B. Conjugates

The present invention also concerns compounds that contain a purine analog pharmacophore conjugated to one or more different chemical entities, such as another purine analog (of the same or different chemical species), a targeting moiety, an antigen or other macromolecule, a peptide recognized by a T cell receptor, etc., as well as to inactivated whole cells or other lipid vesicles. Conjugates can be formed by covalent or non-covalent linkage between the respective active ingredients. Covalent linkages are preferably formed by way of linker molecules. Here the terms "linking group," "linker molecule," "linker," and the like refer to any molecular group useful for linking at least two distinct chemical entities, e.g., a purine analog and a targeting moiety or specific binding molecule. In order to perform the linkage between the chemical entities, it is necessary that each of the reactants contain a chemically complementary reactive group. Examples of complementary reactive groups are amino and carboxyl groups to form amide linkages, carboxy and hydroxy groups to form ester linkages, amino and alkyl halides to form alkylamino linkages, thiols and thiols to form disulfides, or thiols and maleimides or alkylhalides to form thioethers. Hydroxyl, carboxyl, amino, and other functionalities may be introduced by known methods when not already present. If desired, one or more of reactive complementary groups can be "protected", in which event the protected reactive group must be "deprotected" prior to performing the chemistry needed to effect the particular linkage chemistry. Any suitable protection/deprotection scheme can be employed in a particular circumstance. As those in the art will appreciate, any suitable molecular group can be used as a linker, which molecular group is suitable for a particular situation may vary, although it is easily within the skill of those in the art to select or prepare an appropriate molecular group with suitable chemically complementary reactive groups to perform the desired linkage. Regardless of the molecular group selected in a particular circumstance, it preferably provides for stable covalent linkage between the different chemical entities to form a conjugate according to the invention. Specifically, a covalent linkage should be stable relative to the solution conditions under which the linker and linking groups are subjected. Generally, linkers of any suitable length or arrangement can be employed, although linkers that contain about 4-80 carbons, preferably from about 10-70 carbons, more preferably about 10-50 carbons, and even more preferably from about 10-30 carbons or about 10 to 20 carbons, are preferred. Linkers may also contain one or more heteroatoms (e.g., N, O, S, and P) in the molecular linking groups, particularly from 0-10 heteroatoms. The molecular linking group may be branched or straight chain. It will also be appreciated that in some cases, conjugates may be formed directly between a purine analog and targeting moiety or specific binding molecule, in which case a linker is not employed. In such cases, a substituent of the purine analog and a substituent of the specific binding molecule are typically derivatized to provide the complementary reactive groups (one or more which may, if appropriate, be protected) necessary to perform a suitable chemistry to link the different chemical entities.

While covalent linkages are preferred, in some embodiments non-covalent linkages between active ingredients of a conjugate may also be employed to form a conjugate according to the invention. Examples of non-covalent linkages include intermolecular interactions mediated by electrostatic forces, hydrophobicity, etc. For instance, members of a high affinity binding pair can be used to link two or more molecules. Representative examples of high affinity binding pairs include antibodies and antigens, biotin and streptavidin, and cell surface or intracellular receptors and their respective ligands.

A "specific binding molecule" refers to a molecule that binds to a target analyte (e.g., a tissue- or cell-type-specific cell surface receptor) and does not substantially bind to any other molecule present in the sample. By "substantial binding" is meant that binding occurs to an extent sufficient to affect the desired result, i.e., delivery of the conjugate to the target tissue or cell, although a small amount of non-specific binding may occur. In some embodiments the specific binding molecule can be an antibody or an antibody fragment (e.g., the Fab region of an antibody), a ligand for a receptor, a receptor or receptor fragment that binds a ligand, or a member of a high-affinity binding pair (e.g., a biotin-streptavidin pair). A "derivative" is a chemical substance related structurally to another substance and theoretically derivable from it, and in general has the same basic structure as the parent compound.

In different embodiments of the invention, different positions on a purine analog (e.g., positions 289 can be selected as conjugation sites for the linker and specific binding molecule. Conjugation of linker and specific binding molecule at these sites does not substantially adversely affect the ability of the attached purine analog to induce an innate immune response. In this context, an innate immune response is not "substantially adversely affected" if the conjugate retains at least about 10%, preferably at least about 50%, more preferably at least about 75%, and even more preferably at least about 90% of the ability of the unconjugated form of the purine analog to induce an innate immune response in any suitable assay, for example, an in vitro cytokine induction assay. As will be appreciated, different linkers and different linkage chemistries can be used for conjugation at different sites.

After obtaining the desired purine analog and specific binding molecule, they can be conjugated using the particular chemistry needed to link them, directly or through a linker adapted for such purpose. In some embodiments the specific binding molecule is an antibody or antibody fragment. The term "antibody" refers to an immunoglobulin, whether natural or partially or wholly synthetically produced, including derivatives that maintain specific binding ability. The term also covers any protein having a binding domain that is homologous or largely homologous to an immunoglobulin binding domain. An antibody may be monoclonal or polyclonal, and can be a member of any immunoglobulin class (or combination of classes), including any of the human classes: IgG, IgM, IgA, IgD, IgG, and IgE. An "antibody fragment" is any derivative of an antibody that contains less than the complete heavy and light immunoglobulin chains. Preferably, an antibody fragment retains at least a significant portion of the antigen binding domain of at least a heavy or light immunoglobulin chain. Examples of antibody fragments include, but are not limited to, Fab, Fab', F(ab')$_2$, scFv, Fv, dsFv diabody, and Fd fragments.

Antibodies and antibody fragments can be produced using any suitable technique, including production from hybridomas. Antibody fragments can be enzymatically or chemically produced by fragmentation of an intact antibody, or they can be recombinantly produced from one or more nucleic acid molecules that encode the particular antibody fragment sequence(s). Alternatively, antibody fragments can be wholly or partially synthetically produced. As noted above, antibody fragments include single chain antibody fragments, as well as fragments comprising multiple chains, which preferably are linked together, for instance, by disulfide linkages. Antibody fragments can also be multimolecular complexes. A functional antibody fragment typically comprises at least about 50, and often more than about 200, amino acid residues.

A "Fab" fragment is essentially equivalent to that obtained by digestion of immunoglobulins (typically IgG) with the enzyme papain. Fab fragments are preferably recombinantly produced. The heavy chain segment of the Fab fragment is an "Fd" fragment. An "Fab'" fragment is an antibody fragment essentially equivalent to that obtained by reduction of the disulfide bridge or bridges joining the two heavy chains in a F(ab')$_2$ fragment. Fab' fragments are also preferably recombinantly produced. An "Fv" fragment consists of one $V_L$ and one $V_H$ domain held together by non-covalent interactions. The term "dsFv" refers to an Fv with an engineered intermolecular disulfide bond to stabilize a $V_L$-$V_H$ pair. A "F(ab')$_2$" fragment is an antibody fragment essentially equivalent to that obtained from immunoglobulins (typically IgG) by pepsin digestion at pH 4.0-4.5, and is preferably recombinantly produced.

Single-chain Fvs (scFvs) are recombinant antibody fragments consisting of only a variable light chain ($V_L$) and variable heavy chain ($V_H$) covalently linked to each other. Either $V_L$ or $V_H$ may be an amino-terminal domain. The interchain linkage may be accomplished via any suitable linker that connects the two domains without significant steric interference. Typically, such linkers are comprised primarily of stretches of glycine and serine residues with some glutamic acid or lysine residues interspersed for solubility. "Diabodies" are dimeric scFvs. The components of diabodies typically have shorter peptide linkers than most scFvs and they show a preference for associating as dimers.

Active fragments of antibodies (i.e., those that retain a capacity to specifically bind the same antigen as the antibody from which the fragment was derived) preferably include the Fv region of an antibody. Active fragments of antibodies can be made using methods known in the art, such as proteolytic digestion of samples including antibodies. Antibodies may be polyclonal or monoclonal, and include humanized antibodies, unless otherwise specified. A preparation of antibodies can be crude, such as can be prepared from cell culture or whole blood or serum or plasma, or can be partially purified, such as by crude separation methods such as molecular weight purification or ammonium sulfate precipitation, or can be substantially purified, such as by affinity chromatography for a class of antibody, subclass of antibody, or by binding with a particular antigen or epitope. Methods for antibody preparation, production, and purification are known in the art, such as provided by Harlow and Lane, Antibodies, A Laboratory Manual, Cold Spring Harbor (1988).

As will be appreciated, the invention also contemplates conjugates wherein the purine analog is conjugated to an amino acid or peptide. The term "amino acid," comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an -methylbenzyl amide). Other suitable amino and carboxy protecting groups are known to those skilled in the art (See for example, T. W. Greene, *Protective Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine. With regard to peptides, these are typically polymers of amino acid residues, which may be linked by peptide bonds as occur in proteins in nature, by synthetic linkages, or combinations of these. Peptides include those that embody antigenic determinants (such as may be bound by an antibody or a T cell receptor) or structures useful for purification.

Other macromolecules that can be conjugated to a purine analog according to the invention include those that have side chains that increase solubility, such as, for example, groups containing morpholine, piperidine, pyrrolidine, or piperazine rings and the like; polypeptides and proteins; carbohydrates (e.g., polysaccharides), nucleic acids and nucleic acid analogs such as, for example, RNA and DNA with naturally occurring and/or synthetic backbone chemistries (e.g., phosphodiester group modifications (e.g., phosphorothioates, methylphosphonates), 2'-position sugar modifications, 5-position pyrimidine modifications, 7-position purine modifications, 8-position purine modifications, 9-position purine modifications, modifications at exocyclic amines, substitution of 4-thiouridine, substitution of 5-bromo or 5-iodouracil; backbone modifications, methylations, unusual base-pairing combinations such as the isobases, isocytidine and isoguanidine and the like) and/or one or more non-natural bases (e.g., nitroindole), oligonucleotides, peptide nucleic acids (PNAs), and the like; polymers of organic materials, such as, for example, polyethylene glycol, poly-lactide, and the like; monomeric and polymeric lipids; insoluble organic nanoparticles; non-toxic body substances such as, for example, cells, lipids, vitamins, co-factors, antigens such as, for example microbes, such as, for example, viruses, bacteria, fungi, and the like. The antigens can include inactivated whole organisms, or sub-components thereof and the like.

C. Other Forms

The present invention also includes other forms of the compounds of the invention, including prodrug forms. Here, a "prodrug" is a compound that contains one or more functional groups that can be removed or modified in vivo to result in a molecule that can exhibit therapeutic utility in vivo. Examples of two prodrugs according to the invention are represented by Formulas IV and V, below.

Formula IV

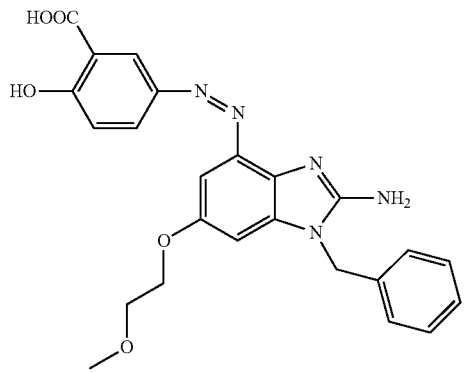

Formula V

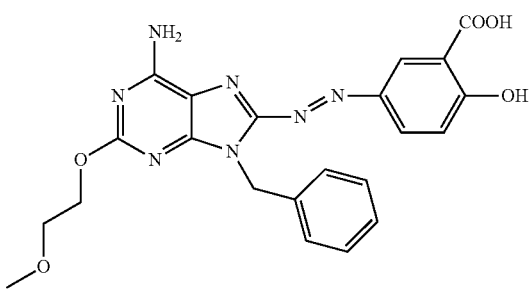

These azo-containing prodrugs can be reductively cleaved by bacteria in a subject's colon to free the TLR agonist represented by Formula VI, below.

Formula VI

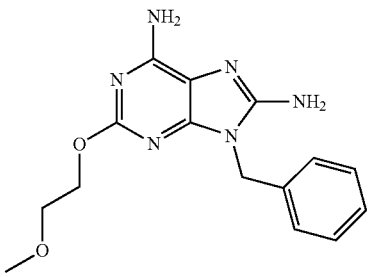

A "polymorph" refers to a compound that has an identical chemical composition (i.e., it is of the same compound species) as compared to another compound but that differs in crystal structure.

D. Synthesis

The compounds of the invention can be synthesized by any suitable method. The synthesis of a preferred class of these compounds derivatized at position 8 of the purine analog are described in Example 2, below.

In the event a compound of the invention has an asymmetric carbon atom, optical isomers exist. As such, the invention encompasses mixtures of the optical isomers, as well as each of the two enantiomer species of such compound. If desired, the resolution of racemic compounds of can be accomplished using conventional means, such as the formation of a diastereomeric salt with an optically active resolving amine; see, for example, "Stereochemistry of Carbon Compounds," by E. L. Eliel (McGraw Hill, 1962); C. H. Lochmuller et al., *J Chromatog.*, 113, 283 (1975); "Enantiomers, Racemates and Resolutions," by J. Jacques, A. Collet, and S. H. Wilen, (Wiley-Interscience, New York, 1981); and S. H. Wilen, A. Collet, and J. Jacques, *Tetrahedron*, 33, 2725 (1977).

The compounds of the invention can also be prepared in the form of their pharmaceutically acceptable salts or their non-pharmaceutically acceptable salts. The non-pharmaceutically acceptable salts are useful as intermediates for the preparation of pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. Preferred carboxylic acid salts are those of hydrophilic amines, such as glucamine or N-($C_1$-$C_4$)alkylglucamine (see, Adger et al. (U.S. Pat. No. 5,811,558)).

2. Compositions

As described throughout this specification, the compounds of the invention are useful as therapeutic agents. The compounds will generally be formulated so as to be amenable to administration to a subject by the chosen route. Thus, a further aspect of this invention concerns compositions, particularly pharmaceutical or veterinary compositions, comprising a TLR agonist, particularly an agonist of TLR7, TLR8, and TLR9, such as, for example, a compound represented by Formula I, or an acceptable salt, base, or prodrug form thereof, formulated together with one or more non-toxic acceptable carriers, preferably pharmaceutically acceptable carriers. The terms "pharmaceutically acceptable carrier" and "physiologically acceptable carrier" refer to molecular entities and compositions that are physiologically tolerable and do not typically produce an unintended allergic or similar untoward reaction, such as gastric upset, dizziness and the like, when administered to a subject. In the context of therapeutic compositions intended for human administration, pharmaceutically acceptable carriers are used. The compounds of the invention may be processed in accordance with conventional methods of pharmaceutical compounding techniques to produce medicinal agents (i.e., medicaments or therapeutic compositions) for administration to subjects, including humans and other mammals, i.e., "pharmaceutical" and "veterinary" administration, respectively. See, for example, the latest edition of Remington's Pharmaceutical Sciences (Mack Publishing Co., Easton, Pa.). Typically, a compound such as a TLR agonist is combined as a composition with a pharmaceutically acceptable carrier. The composition(s) may also include one or more of the following: preserving agents; solubilizing agents; stabilizing agents; wetting agents; emulsifiers; sweeteners; colorants; odorants; salts; buffers; coating agents; and antioxidants.

The compounds of the invention may be prepared as free acids or bases, which are then preferably combined with a suitable compound to yield a pharmaceutically acceptable salt. The expression "pharmaceutically acceptable salts" refers to non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like. Salts also include those from inorganic bases, such as ammonia, hydroxyethylamine and hydrazine. Suitable organic bases include methylamine, ethylamine, propylamine, dimethylamine, diethylamine, trimethylamine, triethylamine, ethylenediamine, hydroxyethylamine, morpholine, piperazine, and guanidine.

In this regard, the compounds, and their respective acid or base salts, can be formulated into liquid, preferably aqueous, formulations for storage and administration, as well as dried formulations that may, for example, be used as powders for intranasal administration or be reconstituted into liquid form just prior to administration to a subject. Liquid pharmaceutically administrable compositions can, for example, be prepared by dissolving, dispersing, etc. the particular active compound and optional pharmaceutical adjuvants in an aqueous carrier. Aqueous carriers include water (particularly water for injection into humans), alcoholic/aqueous solutions, and emulsions and suspensions. Preferred pharmaceutically acceptable aqueous carriers include sterile buffered isotonic saline solutions. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, and inert gases and the like. Non-aqueous solvents may also be included, although when included they preferably comprise less than about 50%, more preferably lass than about 25%, and even more preferably less about 10%, of the total solvent volume of the solution. Examples of non-aqueous solvents include propylene glycol, ethanol, polyethylene glycol, vegetable oils such as olive oil, and injectable organic esters such as ethyl oleate. The pharmaceutical and veterinary compositions of the invention, whether dry or liquid, are preferably formulated for intranasal administration.

If desired, the composition to be administered may also contain minor amounts of nontoxic auxiliary substances such as wetting agents, emulsifying agents, or solubilizing agents, antioxidants, antimicrobials, pH buffering agents and the like, for example, sodium acetate, sodium citrate, cyclodextrin derivatives, sorbitan monolaurate, triethanolamine acetate, triethanolamine oleate, etc. Actual methods of preparing such dosage forms are known, or will be apparent, to those skilled in this art; for example, see Remington: The Science and Practice of Pharmacy, Mack Publishing Company, Easton, Pa., 20th Edition, 2000. The composition or formulation to be administered will, in any event, contain a quantity of the active compound in an amount effective to alleviate the symptoms of the subject being treated.

As those in the art will appreciate, the compositions of the invention may also be formulated for targeted delivery of the active ingredient to a subset of tissues or cells in a subject. In general, targeted delivery is accomplished by formulating a compound of the invention with a targeting moiety. Such moieties include lipids, liposomes, and ligands for molecules that bind, or are bound by, other molecules in vivo.

A composition is comprised of "substantially all" of a particular compound, or a particular form a compound (e.g., an isomer) when a composition comprises at least about 90%, and preferably at least about 95%, 99%, and 99.9%, of the particular composition on a weight basis. A composition comprises a "mixture" of compounds, or forms of the same compound, when each compound (e.g., isomer) represents at least about 10% of the composition on a weight basis. A purine analog of the invention, or a conjugate thereof, can be prepared as an acid salt or as a base salt, as well as in free acid or free base forms. In solution, certain of the compounds of the invention may exist as zwitterions, wherein counter ions are provided by the solvent molecules themselves, or from other ions dissolved or suspended in the solvent.

Generally, the concentration of a compound of the invention in a liquid composition, such as a lotion, will be from about 0.1-25% by weight of the composition, preferably from about 0.5-10% by weight. The concentration in a semi-solid or solid composition such as a gel or a powder typically is about 0.1-5% by weight, preferably about 0.5-2.5% by weight.

The amount of the compound required for use in treatment will vary not only with the particular compound and salt selected, but also with the route of administration, the nature of the condition being treated, and the age and condition of the patient, among other factors, and ultimately is determined at the discretion of the attending physician or clinician. The desired dose may conveniently be presented in a single dose or as divided doses administered at appropriate intervals, for example, as two, three, four or more sub-doses per day. The sub-dose itself may be further divided, for example, into a number of discrete, loosely spaced administrations, such as multiple inhalations from an insufflator or by application of a plurality of drops into the eye.

3. Administration

The compounds of this invention are administered in a therapeutically effective amount to a subject in need of treatment. Administration of the compositions of the invention can be via any of suitable route of administration, particularly parenterally, for example, intravenously, intra-arterially, intraperitoneally, intrathecally, intraventricularly, intraurethrally, intrasternally, intracranially, intramuscularly, or subcutaneously. Such administration may be as a single bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives. The preparation of suitable, and preferably sterile, parenteral formulations is described in detail in the section entitled "Compositions", above.

In the context of this invention, actual dosage levels for the compositions of this invention can be varied so as to obtain an amount of the active compound(s) that is effective to achieve the desired therapeutic response for a particular patient, compositions and mode of administration. In general, daily administration or continuous infusion at dosages less than those known to produce toxicities will be the preferred therapeutic protocol to enhance the activity of the drug. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

With regard to human and veterinary treatment, the amount of a particular composition that is administered will, of course, be dependent on a variety of factors, including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; the judgment of the prescribing physician or veterinarian; and like factors well known in the medical and veterinary arts.

The term "effective amount" of a compound (or composition, or the like) means an amount that is effective to exhibit the desired biological activity or achieve the desired clinical result in a subject response to the particular treatment, commensurate with a reasonable benefit/risk ratio when used in the manner of this invention.

A "therapeutically effective amount" refers to an amount of an active ingredient sufficient to effect treatment when administered to a subject in need of such treatment. In the context of cancer treatment, a "therapeutically effective amount" is one that produces an objective response in evaluable patients. Such responses include changes in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc., as well as the cessation or regression in growth determined against clinically accepted standards. With reference to these standards, determination of therapeutically effective dosages of a composition comprising a purine analog according to the invention may be readily made by those of ordinary skill in the art. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy The term "treatment" or "treating" means any treatment of a disease or disorder, including preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "protection" thus includes "prophylaxis".

As used herein with respect to cancer or cancer cells, the term "inhibition" or "inhibit" includes both the reduction in cellular proliferation, blockage of cellular proliferation, or killing some or all of said cells. Thus, the term can be used in both the context of a prophylactic treatment to prevent development of cancer or as a treatment that will block, or slow the spread of established cancer or other disease or disorder.

As used herein "treating" includes (i) preventing a pathologic condition from occurring (e.g., prophylaxis) or symptoms related to the same; (ii) inhibiting the pathologic condition or arresting its development or symptoms related to the same; and (iii) relieving the pathologic condition or symptoms related to the same.

As used herein "in combination with" or "administered in conjunction with" includes simultaneous administration, separate administration or sequential administration of at least two active agents in a manner that allows the desired beneficial effect to occur.

Representative examples of combination therapies include those that involve the administration of a composition containing a compound of the invention (including conjugates thereof) in combination with an inhibitor of inosine monophosphate dehydrogenase (IMPDH). Here, an "IMPDH inhibitor" refers to an inhibitor of the enzyme inosine monophosphate dehydrogenase, of which there are at least three in clinical use: ribavirin, mizoribine, and mycophenolate mofetil. Ribavirin and mizoribine are prodrugs that are phosphorylated intracellularly to produce IMP analogs. Viramidine is a prodrug of Ribavirin. Mycophenolate mofetil is immunosuppressive, and has gastrointestinal irritative properties that may be attributable to enterohepatic recirculation. Mizoribine aglycone, a prodrug, is used as an IMPDH inhibitor. Other non-limiting examples IMPDH inhibitors, including prodrugs of mizoribine and mizoribine aglycone, are known See, e.g., published U.S. Patent application No. 20050004144. Other combination therapies include the combination of a compound of the invention with a therapeutic regimen that employs a chemotherapeutic agent, alone or in conjunction with other therapies such as radiation treatment and/or surgery, in order to treat a cancer. Similarly, a compound according to the invention can be combined with an antimicrobial agent to treat an infection caused by a pathogenic microorganism (e.g., a pathogenic bacteria, fungus, protozoan, or virus).

The magnitude of a prophylactic or therapeutic dose of a compound or compounds of formula (I) in the acute or chronic management of cancer, e.g., prostate cancer, will vary with the type and/or stage of the cancer, the adjunct chemotherapeutic agent(s) or other anti-cancer therapy used, and the route of administration. The dose, and perhaps the dose frequency, will also vary according to the age, body weight, condition, and response of the individual patient. In general, the total daily dose range for a compound or compounds of formula (I), for the conditions described herein, is from about 50 mg to about 5000 mg, in single or divided doses. Preferably, a daily dose range should be about 100 mg to about 4000 mg, most preferably about 1000-3000 mg, in single or divided doses, e.g., 750 mg every 6 hr of orally administered compound. This can achieve plasma levels of about 500-750 uM, which can be effective to kill cancer cells. In managing the patient, the therapy should be initiated at a lower dose and increased depending on the patient's global response.

Any suitable route of administration may be employed for providing the patient with an effective dosage of a compound of formula (I), including conjugates thereof. For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The compound may be administered prior to, concurrently with, or after administration of chemotherapy, or continuously, i.e., in daily doses, during all or part of, a chemotherapy regimen. The compound, in some cases, may be combined with the same carrier or vehicle used to deliver the anti-cancer chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. Tablets, capsules, pills, granules, microparticles and the like can also comprise an enteric coating, such as a coating of one of the Eudragit® polymers, that will permit release of the active compound(s) in the intestines, not in the acidic environment of the stomach.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds may be applied in liquid or cream-based formulations, which preferably will include a dermatologically acceptable carrier, which may be a solid, gel, or liquid. Useful solid carriers include finely divided solids such as talc, clay, microcrystalline cellulose, silica, alumina and the like. Useful liquid carriers include water, alcohols, or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses, and/or modified mineral materials can also be employed with liquid carriers to form spreadable pastes, gels, ointments, soaps, and the like, for application directly to the skin of the user.

Useful dosages of the compounds of the invention can be determined by comparing their in vitro activity, and in vivo activity in animal models. Methods for the extrapolation of effective dosages in mice, and other animals, to humans are known to the art. See, e.g., U.S. Pat. No. 4,938,949.

Other drugs or treatments, including treatment with other chemotherapeutic agents, irradiation or other anti-cancer agents such as alkylating agents, anti-tumor antibodies, or cytokines, can be used with the present compounds. See, e.g., Remington's Pharmaceutical Sciences (18$^{th}$ ed. 1990) at pages 1138-1162.

4. Applications

As described above, certain aspects of the invention relate to compositions that contain a compound of the invention, which compositions are useful in the treatment or prevention of a disease or disorder in, for example, humans or other mammals (e.g., bovine, canine, equine, feline, ovine, and porcine animals), and perhaps other animals as well. Specifically, this invention enables the treatment of cells, e.g., cancer cells, with the compounds of the invention. Depending on the particular compound, the composition will, for example, be useful for treating cancer, an infection, enhancing adaptive immunity (e.g., antibody production, T cell activation, etc.), as vaccines, and/or stimulating the central nervous system.

In the context of cancer, it is worth noting that a major obstacle to effective cancer therapy concerns the dose-limiting toxicity of many cytotoxic drugs, including the vinca alkaloids (e.g., vinblastine), the anthracyclines (e.g., doxorubicin), the epipodophyllotoxins (e.g., etoposide), the taxanes (e.g., taxol), antibiotics (e.g., actinomycin D), antimicrotubule drugs (e.g., colchicine), protein synthesis inhibitors (e.g., puromycin), toxic peptides (e.g., valinomycin), topoisomerase inhibitors (e.g., topotecan), DNA intercalators (e.g., ethidium bromide), and anti-mitotics.

An "alkylating agent" refers to a chemotherapeutic compound that chemically modifies DNA and disrupts its function. Some alkylating agents cause formation of cross links between nucleotides on the same strand, or the complementary strand, of a double-stranded DNA molecule, while still others cause base-pair mismatching between DNA strands. Exemplary alkylating agents include bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine. An "anti-metabolite" refers to a chemotherapeutic agent that interferes with the synthesis of biomolecules, including those required for DNA synthesis (e.g., nucleosides and nucleotides) needed to synthesize DNA. Examples of anti-metabolites include capecitabine, chlorodeoxyadenosine, cytarabine (and its activated form, ara-CMP), cytosine arabinoside, dacabazine, floxuridine, fludarabine, 5-fluorouracil, gemcitabine, hydroxyurea, 6-mercaptopurine, methotrexate, pentostatin, trimetrexate, and 6-thioguanine. An "anti-mitotic" refers to a chemotherapeutic agent that interferes with mitosis, typically through disruption of microtubule formation. Examples of anti-mitotic compounds include navelbine, paclitaxel, taxotere, vinblastine, vincristine, vindesine, and vinorelbine. An "intercalating agent" refers to a chemotherapeutic agent that inserts itself between adjacent base pairs in a double-stranded DNA molecule, disrupting DNA structure and interfering with DNA replication, gene transcription, and/or the binding of DNA binding proteins to DNA In the context of cancer therapy, the compounds of the present invention may be used alone, i.e., in monotherapy (refers to a treatment regimen based on the delivery of one therapeutically effective compound, whether administered as a single dose or several doses over time), or in combination with other therapeutic agents or other anti-cancer therapies (e.g., radiation, surgery, bone marrow transplantation, etc.), as well as to potentiate the effects of other therapies, including treatment with other chemotherapeutic agents. As will be appreciated, "combination therapy" (in the context of cancer and other therapies) and the like refer to a course of therapy that involves the provision of at least two distinct therapies to achieve an indicated therapeutic effect. For example, a combination therapy may involve the administration of two or more chemically distinct active ingredients, for example, a fast-acting chemotherapeutic agent and a myeloprotective agent. The agents may be delivered or may be administered as part of the same composition or as different compositions according to the same therapeutic regimen or different regimens, depending on the active ingredients involved, the disease to be treated, the age and condition of the patient, etc. Moreover, when used in combination with another therapeutic agent, the administration of the two agents may be simultaneous or sequential. Simultaneous administration includes the administration of a single dosage form that comprises both agents, and the administration of the two agents in separate dosage forms at substantially the same time. Sequential administration includes the prior, concurrent, or subsequent administration of the two or more agents according to the same or different schedules, provided that there is an overlap in the periods during which the treatment is provided. Alternatively, a combination therapy may involve the administration of one or more chemotherapeutic agents as well as the delivery of radiation therapy and/or surgery or other techniques to either improve the quality of life of the patient or to treat the cancer. When one or more chemotherapeutic agents are combined with, for example, radiation and/or surgery, the drug(s) may be delivered before or after surgery or radiation treatment.

An advantage afforded by the compounds of the invention in the treatment of cancer relates to their ability to elicit or enhance an innate immune response following administration in an effective amount of the compound.

Beyond cancer, compounds of the invention can also be used to treat or prevent infections caused by pathogenic microorganisms, include bacteria, yeast, viruses, and protozoa, to prepare vaccines against pathogenic bacteria, fungi, protozoa, viruses, and cancer cells, as well as to stimulate the innate immune system or enhance the effectiveness of monoclonal antibodies to treat or prevent cancer. In representative embodiments of this therapeutic aspect of the invention, pathological conditions or symptoms in a mammal, such as a human, can be prevented or treated, as the case may be, by administering to a mammal in need of such therapy an amount of a TLR agonist of the invention, or conjugate containing such an agonist, effective to achieve the intended result, as determined by the attending physician or veterinarian. Non-limiting examples of pathological conditions or symptoms that are suitable for treatment in accordance with the invention include cancers, bacterial, fungal, or viral diseases, and autoimmune diseases. Viral diseases amenable to such treatment include those caused by DNA and RNA viruses. Indeed, treatment or prevention of a viral disease caused by hepatitis C or hepatitis B virus, a coronavirus (e.g., the virus that causes Severe Acute Respiratory Syndrome (SARS)), an influenza virus, . Representative autoimmune diseases treatable in accordance with the invention multiple sclerosis, lupus, rheumatoid arthritis, Crohn's Disease, and the like

EXAMPLES

The invention will be further described by reference to the following detailed examples. These Examples are in no way to be considered to limit the scope of the invention in any manner.

Example 1

Biological Assays Using Bone Marrow-Derived Macrophages (BMDM)

Bone marrow was isolated from the femora and tibia of C57BL/6 mice. Cells were plated on non-tissue culture-treated petri dishes and cultured in DMEM high glucose medium supplemented with 10% fetal bovine serum (FBS), L-glutamine, penicillin/streptomycin (all from Invitrogen, San Diego, Calif.), and 30% L929 cell-conditioned media. Cells were grown at 37° C., 5% $CO_2$ for 7 days without replacing the medium. Macrophages were then harvested by gentle scraping, counted, and re-plated under various conditions.

For studies on cytokine production, 7-day-old BMDM were seeded in 96-well plates at a density of $5 \times 10^4$ cells per well and grown for another 3 days before stimulation with various compounds.

Example 2

Synthesis of Position 8-Substituted Compounds

This example describes the synthesis of several compounds of the invention that were derivatized at the position 8 carbon of the purine. These compounds are represented by Formula VII.

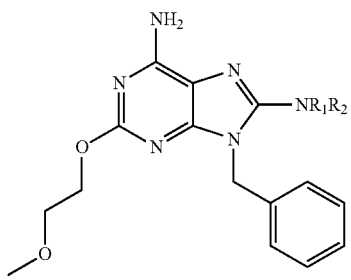

Formula VII

Several of the compounds produced in accordance with these procedures are listed in the Table 1, below:

TABLE 1

| Entry | $R_1$ | $R_2$ | Reaction method |
|---|---|---|---|
| 1 | H | H | E |
| 2 | H | Me | A |
| 3 | H | Et | A |
| 4 | H | Pr | A |
| 5 | H | Bu | A |
| 6 | Et | Et | A |
| 7 | H | 2-Hydroxylethyl | A |
| 8 | 2-Hydroxylethyl | 2-Hydroxylethyl | B |
| 9 | H | 3-Hydroxypropyl | A |
| 10 | 3-Hydroxypropyl | 3-Hydroxypropyl | B |
| 11 | H | 4-hydroxylbutyl | A |
| 12 | H | Tetrahydrofurfuryl | A |
| 13 | H | 2-Furfuryl | D |
| 14 | H | Benzyl | B |
| 15 | H | Hydroxyl | — |
| 16 | O | O | — |
| 17 | H | Morpholinoethyl | A |
| 18 | H | Piperidinoethyl | A |
| 19 | H | Methoxyethyl | A |
| 20 | H | Diethanolaminoethyl | A |

TABLE 1-continued

| Entry | $R_1$ | $R_2$ | Reaction method |
|---|---|---|---|
| 21 | H | Diethanolaminopropyl | A |
| 22 | H | Cyclohexylmethyl | A |
| 23 | | Morpholino | C |
| 24 | H | Acetyl | F |
| 25 | H | Ethyoxycarbonyl | F |

The general synthetic scheme used to generate these compounds was as follows:

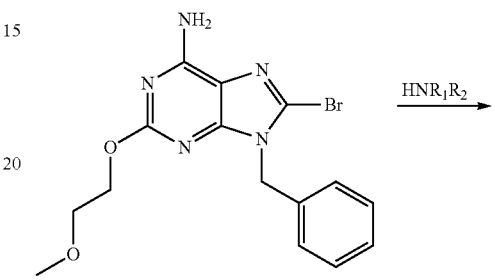

8-Bromo compound
Formula VIII

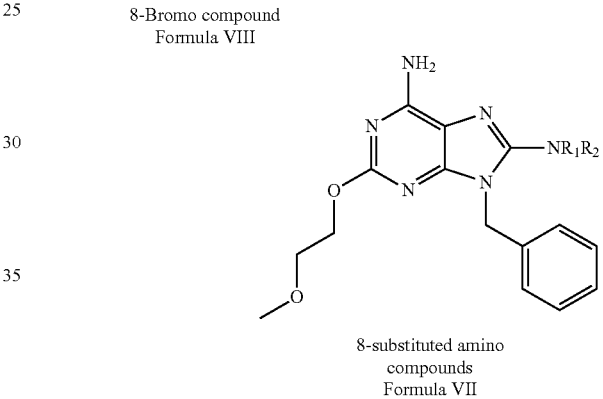

8-substituted amino compounds
Formula VII

In each synthesis, the 8-Bromo compound was 6-amino-9-benzyl-2-(2-methoxyethoxy)purine. See U.S. Pat. No. 6,329,381 for a description of this intermediate and its synthesis.

A. Method A

A quantity of the 8-Bromo intermediate compound (78 mg, 0.2 mmol) and the appropriate amine (1 g) were mixed in water (3 mL). The mixture was heated at 115-125° C. in a sealed steel reaction vessel for 12 to 24 hr. and concentrated in vacuo. The residue was subjected to column chromatography (silica gel; eluent, dichloromethane-methanol, 10:1 (vol/vol)) to yield the corresponding 8-substituted amino compound (see Table 1, above). Example: 8-(3-hydroxypropyl) amino derivative (Table 1, Entry 9).

$^1$H-NMR (500 MHz, $CDCl_3$) δ 7.18-7.33 (m, 5 H), 5.11 (br, 4 H), 4.44 (t, J=5 Hz, 2 H), 3.73 (t, J=5 Hz, 2 H), 3.52 (m, 4 H), 3.40 (s, 3 H), 1.61 (m, 2 H). MS (ESI) m/z: 373.8 $(M+H^+)$. Mp: 128-130° C.

B. Method B

A quantity of the 8-Bromo compound (50 mg, 0.132 mmol) was added to the high-boiling amine (1.5 mL) and the mixture was heated at 160° C. for 4 hr. The reaction was cooled to room temperature (RT) and poured into ethyl ether (15 mL); the precipitate was filtered off. The filtrate was concentrated and the crude product was purified as in method A to yield the corresponding 8-substituted amino compound (35 mg, 65.6%) as white solid. Example: 8-benzylamino derivative (Table 1, Entry 14). $^1$H-NMR (500 MHz, CDCl$_3$) δ 7.01-7.36 (m, 10 H), 5.66 (br, 2 H), 5.21 (s, 2 H), 4.65 (d, J=5 Hz, 2 H), 4.49 (t, J=5 Hz, 2 H), 3.73 (t, J=5 Hz, 2 H), 3.38 (s, 3 H). MS (ESI) m/z: 405.5 (M+H$^+$). Mp: 134-136° C.

C. Method C

A quantity of the 8-Bromo compound (20 mg, 0.052 mmol) was mixed with Pd$_2$(dba)$_3$ (1 mg), BINAP (10 mg), morpholine (3 mL), and K$_2$CO$_3$ (30 mg) in t-butanol (6 mL). The mixture was heated at 130° C. for 12 hr. The reaction was cooled to room temperature and then filtered. The filtrate was concentrated and the residue was purified by chromatography (silica gel; eluent: dichloromethane-methanol, 10:0.5 (vol/vol)) to yield compound the 8-morpholino derivative (10 mg, 50%) as a white solid. Example: 8-morpholino derivative (Table 1, Entry 23)

$^1$H-NMR (500 MHz, CDCl$_3$) δ 7.22-7.29 (m, 5 H), 5.26 (br, 2 H), 5.18 (s, 2 H), 4.42 (t, J=5 Hz, 2 H), 3.73 (m, 6 H), 3.39 (s, 3 H), 3.07 (m, 4 H). MS (ESI) m/z: 385.4 (M+H$^+$). Mp: 130-132° C.

D. Method D

A quantity of the 8-Bromo compound (50 mg, 0.16 mmol) and furfuraldehyde (15.4 mg, 0.16 mmol) were combined in methanol (5 mL), and NaCNBH$_3$ (30.3 mg, 0.48 mmol) and acetic acid (10 mg) were then added. The reaction was stirred at room temperature for 24 hr. and the solvent was distilled off in vacuo. The residue was mixed with water (10 mL) and dichloromethane (10 mL) and stirred at room temperature for 30 min. The organic phase was separated. The water was neutralized with acetic acid to pH 6 and extracted with dichloromethane (2×5 mL) and the combined organic phase and extracts were washed with water (10 mL) and brine (10 mL), and dried. The solvent was distilled and the residue was purified by chromatography (silica gel, eluent: dichloromethane) to yield the furfuryl compound as a white solid.

E. Method E

A quantity of the 8-Bromo compound (50 mg, 0.132 mmol) was dissolved in DMF (5 mL) and NaN$_3$ (26 mg, 0.4 mmol) was added. The mixture was heated and stirred at 75° C. for 6 hr. and cooled to room temperature. The solvent was distilled off in vacuo and the residue was dissolved in methanol (10 mL). Palladium on charcoal (10%, 10 mg) was added and the mixture was hydrogenated for 12 hr. at room temperature (1 atm). The catalyst was filtered off and solvent was distilled in vacuo. The residue was purified by chromatography (silica gel, eluent: dichloromethane-methanol, 10:1 (vol/vol)) to yield the 8-amino compound (Formula X, below) as white solid.

$^1$H-NMR (400 MHz, d$^6$-DMSO) δ 7.21-7.28 (m, 5 H), 6.40 (br, 2 H), 6.21 (br, 2 H), 5.07 (s, 2 H), 4.22 (t, J=4 Hz, 2 H), 3.55 (t, J=4 Hz, 2 H), 3.23 (s, 3 H). MS (ESI) m/z: 315.0 (M+H$^+$). Mp: 187-189° C. (dec).

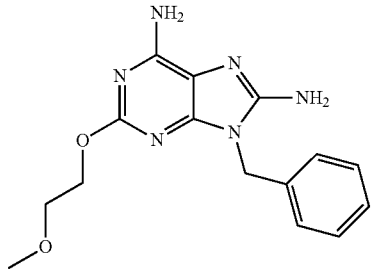

Formula X

A HCl salt of this 8-amino compound was then prepared by dissolving the compound in methanol and acidifying the mixture to pH 2 a HCl-dioxane solution. The HCl salt of the 8-amino compound was obtained quantitatively as a white solid after all solvent was evaporated in vacuo.

F. Method F

A quantity of the 8-amino compound (0.1 mmol) described in Part (E) of this Example was dissolved in dry DMF (5 mL), after which pyridine (1 mL), acetyl chloride (0.1 mmol), and DMAP (0.02 mmol) were added. The mixture was stirred at room temperature for 16 hr. The solvent was removed in vacuo and the crude product was purified by chromatography (silica gel; eluent: dichloromethane-methanol 10:1 (vol/vol)) to yield the 8-acetamido compound as a white solid.

Example 3

Synthesis and Immunostimulatory Activity of 8-Substituted Amino-9-benzyladenines as Potent Toll-Like Receptor 7 Agonists This example describes the synthesis and testing of several 9-benzyl adenine derivatives bearing various substituted amines at the 8-position of the purine analog. These compounds were evaluated for interferon induction in PBMC from healthy human donors. In these experiments, the 8-bromo adenine derivative, compound 5 (Formula VIII, above), was used as a versatile intermediate for all substitutions. The most active 8-susubstituted amino compound was found to be the 8-morpholinoethylamino derivative (compound 19), which had an EC$_{50}$ in the submicromolar range.

It was known from earlier studies that certain guanosine analogs activate immune cells via TLR7 (Lee, et al., supra), and that a sugar moiety was not required for immune system potentiation, as certain alkylated purines were also effective at stimulating TLR7 activity. Michael, et al. (1993), J. Med. Chem., vol. 36: 3431-3436. Since then, alkylated adenine derivatives have been discovered that are even more potent interferon inducers than the guanines and guanosines. Isobe, et al (2006),), J. Med. Chem., vol. 49: 2088-2095; Kurimoto, et al. (2004), Chemical & Pharmaceutical Bulletin, vol. 52: 466-469; Kurimoto, et al. (2004), Bioorganic & Medicinal Chemistry, vol. 12: 1091-1099. Recent studies indicate that TLR7-mediated immunity against HCV involves at least two mechanisms: one depends on type 1 interferon production by leukocytes; the other is mediated by TLR7 expressed by virally infected hepatocytes. Lee, et al. (2006), PNAS, vol. 103: 1828-1833. Ideal TLR agonists will have the appropriate balance of innate immune system activation and patient tolerance.

A series of 8-substitutedamino adenine compounds were designed, prepared, and evaluated in mouse and human cell based assays. The starting point for the design of the compounds was based on recent reports describing the potent activity of 9-benzyl-8-oxo-2-alkoxyadenines as interferon inducers. Kurimoto, et al. (2004), Chemical & Pharmaceutical Bulletin, supra; Kurimoto, et al. (2004), Bioorganic & Medicinal Chemistry, supra. The first compound prepared was 9-benzyl-2-methoxyethoxy-8-oxoadenine, which was synthesized according to a published procedure. Kurimoto, et al. (2004), Bioorganic & Medicinal Chemistry, supra. The compound was then confirmed to be signalling exclusively through TLR7. Lee, et a; (2006), supra. A review of the literature revealed that apart from the 8-oxo group, no other modifications at the 8 position had been reported for this purine class of interferon inducers, with the exception of a few prodrugs that would eventually provide the 8-oxo function. Kurimoto, et al. (2004), Chemical & Pharmaceutical Bulletin, supra. Thus, the reported modifications included those at the 2 and 9 positions only. Accordingly, it was decided to to prepare and investigate the structure activity function of a series of 8-substituted amino adenines while maintaining all other structural features constant. The versatile 8-bromo adenine derivative (compound 5; Formula VIII, above) was used as an intermediate for all substitutions. The general procedures for the amine substitutions are depicted in Scheme 1, below, and the final products are listed in Table 2, each with the corresponding method of preparation indicated.

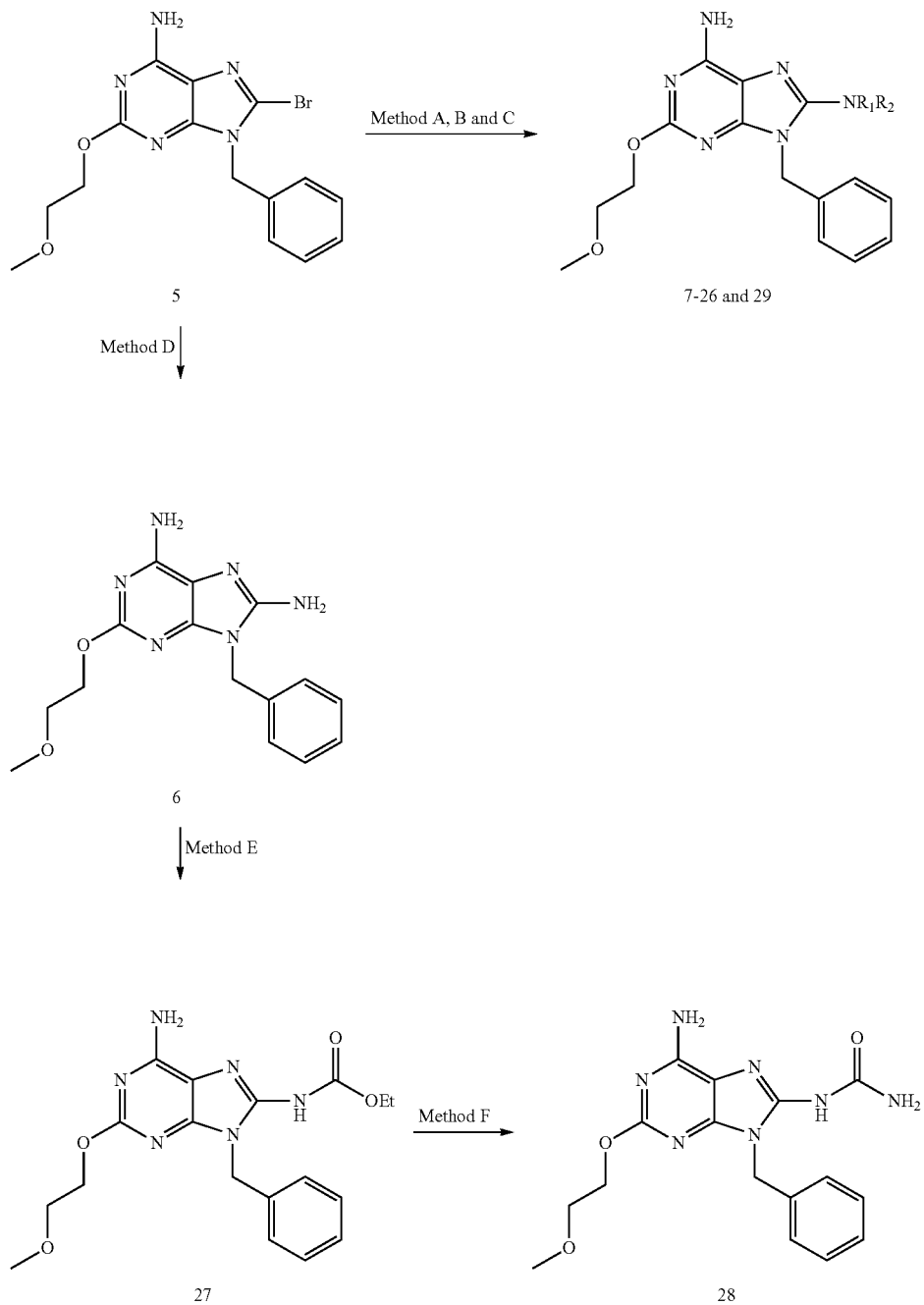

Scheme 1

Reagents and conditions: Method A) NH(R$_1$R$_2$), H$_2$O, 110--125° C., 12 hr. Method B) NH(R$_1$R$_2$), 150--160° C., 6 hr. Method C) pd$_2$(dba)$_3$, BINAP, secondary amine, K$_2$CO$_3$, t-butanol, 130° C., 12 hr. Method D) (1) NaN$_3$, DMF, 100° C., 7 hr.; (2) H$_2$/R-Ni, RT, 12 h. Method E) ClCOOEt, pyridine, RT, 12 h. Method F) NH$_3$/MeOH, 70° C., 10 hr.

TABLE 2

Formula VII

[Structure: purine with $NH_2$ at 6-position, 2-methoxyethoxy group at 2-position, N-benzyl at 9-position, and $NR_1R_2$ at 8-position]

| Cmpd | $R_1$ | $R_2$ | Method | IFN-α[a] | SEM |
|---|---|---|---|---|---|
| 4 | | | | 418.00 | 53.94 |
| 6 | H | H | D | 35.25 | 23.19 |
| 7 | H | Me | A | b | |
| 8 | H | Et | A | 80.30 | 34.22 |
| 9 | H | n-Pr | A | 8.80 | 4.44 |
| 10 | H | n-Bu | A | 0.73 | 0.73 |
| 11 | Et | Et | C | b | |
| 12 | H | 2-Hydroxyethyl | A | 99.21 | 36.11 |
| 13 | 2-Hydroxyethyl | 2-Hydroxyethyl | B | 0.82 | 0.00 |
| 14 | H | 3-Hydroxy-n-propyl | A | 113.18 | 39.73 |
| 15 | H | 4-hydroxy-n-butyl | A | b | |
| 16 | H | Tetrahydrofurfuryl | A | b | |
| 17 | H | Benzyl | B | b | |
| 18 | H | Phenylethyl | A | 1.33 | 0.00 |
| 19 | H | 2-(Morpholino)ethyl | A | 110.48 | 30.16 |
| 20 | H | 2-(Piperidin-1-yl)ethyl | A | b | |
| 21 | H | 2-Methoxyethyl | A | b | |
| 22 | H | Diethanolaminoethyl | A | b | |
| 23 | H | Diethanolaminopropyl | A | b | |
| 24 | H | Cyclohexylmethyl | A | b | |
| 25 | | Morpholino | C | 0.41 | 0.00 |
| 26 | H | 2-(1H-Indol-3-yl)ethyl | A | b | |
| 27 | H | Ethoxycarbonyl | E | 1.03 | 0.00 |
| 28 | | Carbamoyl (8-Ureido) | F | b | |
| 29 | H | $NH_2$ (8-Hydrazino) | A | 0.21 | 0.21 |
| DMSO | | | | 0.26 | 0.26 |

[a] Interferon concentration in pg/mL. All compounds tested at 1 μM;
[b] Below lower limit of detection.

The synthesis of compounds 7-10, 12, 14-16, 18-24, 26 and 29, above, by method A was carried out in an autoclave using water as solvent. The hydrazino compound 29 precipitated from a reaction using 20% aqueous hydrazine while compound 6 was the major product if a concentration of hydrazine lower than 10% was used. Products 13 and 17 were afforded by reaction of 5 with a large excess of diethanolamine or benzylamine, respectively, as reagent and solvent at elevated temperatures. Compounds 11 and 25 were obtained in good yield by the palladium-catalyzed reaction of the corresponding secondary amine with compound 5 under anhydrous conditions, the first such palladium-catalyzed amination of an adenine system by a hindered amine. Methods for 8-aminoadenine preparation have been reported. Holmes & Robins (1965), J. Am. Chem. Soc., vol. 87: 1772-1776; Young, et al. (1990), J. Med. Chem., vol. 33: 2073-2080; Janeba, et al. (2001), Collection of Czechoslovak Chemical Communications, vol. 66: 517-532.

Reaction of 8-bromo compound 5 with $NaN_3$ followed by Raney-Ni catalyzed hydrogenation furnished compound 6 in good yield. Acylation of compound 6 with ethylchloroformate led to the ethylcarbamate, compound 27, which was converted to the ureido compound 28 by reaction with methanolic ammonia. All compounds were tested for their ability to induce the production of interferon α in human PBMC compared to compound 4 as a positive control. Human blood samples were obtained from the San Diego Blood Bank. Peripheral blood mononuclear cells (PBMC) were isolated by density-gradient centrifugation over Ficoll-Hypaque (Amersham Pharmacia). Cells were resuspended in RPMI 1640 medium, supplemented with 10% fetal bovine serum (FBS), L-glutamine, and penicillin/streptomycin (RP10; Invitrogen, Carlsbad, Calif.), plated at $10^6$ cells/well in 96-well plates, and stimulated with compounds at 1 μM final concentration for 24 hr. at 37° C., 5% $CO_2$. The IFN-α level in the supernatants was measured by Luminex (Austin, Tex.) using the Beadlyte Human MultiCytokine kit (Upstate, Charlottesville, Va.), according to the manufacturer's instructions. Results presented in Table 2 are averages of data composited from four different donors. As indicated in Table 2, each compound was tested at 1 μM and the most active compounds were found to be compounds 8, 12, 14, and 19. Detailed analytical data for these compounds is as follows:

In addition, the $EC_{50}$ (the concentration of compound at which 50% of the maximal IFN concentration was achieved) was determined for these four most active compounds, and these data are shown relative to compound 4 in Table 3, below.

TABLE 3

$EC_{50}$ Data

| Compound | $EC_{50}$ (μM) |
|---|---|
| 4 | 0.14 |
| 6 | >10 |
| 8 | 4.42 |
| 12 | 5.33 |
| 14 | 3.20 |
| 19 | 0.79 |

For this dose response study, cells were treated with the listed compounds at concentrations ranging from 10 μM to 10 nM for 24 hr. The data shown in Table 3 are composited from three different donors, and a non-linear regression curve fit analysis was performed using GraphPad Prism software version 4.0b (San Diego, Calif.) to determine the $EC_{50}$.

The simple replacement of the 8-oxo function in compound 4 with an amino group (compound 6) completely removed all interferon inducing activity. However, further substitution of this amino function yielded several active compounds structure-activity trends that are apparent even within this relatively small group. First, the homologous series of N-methyl, N-ethyl, N-n-propyl, and N-n-butyl derivatives showed that, by comparison, the 2-carbon chain (compound 8) was superior to the others. However, when second ethyl group was added (compound 11), the activity is lost. When a terminal hydrophilic group, such as OH, was added to the ethyl group (compound 12), the activity was enhanced somewhat. In this series, the hydroxypropyl was about equally active, but the hydroxybutyl was devoid of activity. Addition of a second hydroxyalkyl group (compound 13) again abrogated activity. The ring-containing secondary amine, morpholino compound 25, was also not active. Interestingly, addition of a 2-carbon alkyl chain between the 8-amino and the morpholino ring (compound 19) resulted in the highest activity of this entire group of 8-substituted amino compounds, with an $EC_{50}$ of 0.79 μM. Other compounds with ring-chain combinations besides morpholinoethyl, such as phenylethyl (18), piperidin-1-ylethyl (compound 20), and 2-(1H-Indol-3-yl)ethyl (compound 26) were not active.

All patents, patent applications, and publications mentioned in the specification are indicative of the levels of those of ordinary skill in the art to which the invention pertains. Each patent, patent application, and publication cited herein is hereby incorporated by reference in its entirety for all purposes regardless of whether it is specifically indicated to be incorporated by reference in the particular citation.

All of the compounds, compositions, and methods disclosed and claimed herein can be made and executed without undue experimentation in light of the present disclosure. Moreover, it is intended to obtain rights which include alternative and/or equivalent embodiments to the extent permitted, including alternate, interchangeable, and/or equivalent structures, functions, ranges, or steps to those claimed, whether or not such alternate, interchangeable and/or equivalent structures, functions, ranges, or steps are disclosed herein, and without intending to publicly dedicate any patentable subject matter, as it is intended that all patentable subject matter disclosed herein eventually be the subject of patent claims.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Also, the invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Furthermore, while the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed:

1. A compound having formula II:

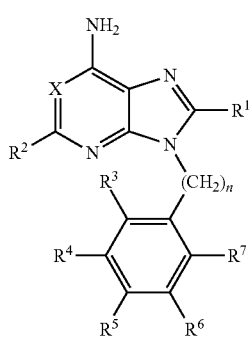

Formula II wherein:
X is nitrogen;
$R^1$ is a moiety selected from the group consisting of a nitro, cyano, hydroxylamino, alkoxylamino, unsubstituted hydrazino $NR^9R^{10}$, $NHCOR^{11}$ and $NHCOOR^{11}$;
$R^9$ and $R^{10}$ each are independently selected from the group consisting of hydrogen, $C_{1-8}$alkyl, $C_{3-6}$cycloalkyl, $C_{1-6}$alkyloxy$C_{1-6}$alkyl, carbonyloxy$C_{1-6}$alkyl, mono- or di($C_{1-6}$alkyl)amino$C_{1-6}$alkyl, mono- or di-(hydroxy $C_{1-6}$alkyl)amino$C_{1-6}$alkyl), aryl$C_{1-6}$alkyl, and heteroaryl$C_{1-6}$alkyl, each optionally substituted with 1 or 2 substituents each independently selected from the group consisting of $C_{3-6}$cycloalkyl, hydroxyl, $C_{3-6}$heteroaryl, $C_6$aryl and $C_{3-6}$ heterocycloalkyl; or
$R^9$ and $R^{10}$ form an optionally substituted pyrrolidinyl, piperidinyl, homopiperidinyl, morpholino or thiomorpholino group when taken together with the nitrogen atom to which they are attached;
$R^{11}$ is a moiety selected from the group consisting of $C_{1-6}$alkyl and substituted alkyl;
$R^2$ is $OR^{12}$ or $SR^{12}$;
$R^{12}$ and $R^{13}$ each is a moiety independently selected from the group consisting of hydrogen, $C_{1-8}$ alkyl, $C_{1-6}$alkyloxy$C_{1-6}$alkyl, carbonyloxy$C_{1-6}$alkyl, mono- or di($C_{1-6}$alkyl)amino$C_{1-6}$alkyl, mono- or di(hydroxy$C_{1-6}$alkylamino$C_{1-6}$alkyl, aryl$C_{1-6}$alkyl, and heteroaryl$C_{1-6}$ alkyl; and
$R^3$ and $R^7$ each is a moiety independently selected from the group consisting of hydrogen, cyano, $R^{12}$, $OR^{12}$, $SR^{12}$ and $NR^{12}R^{13}$, $COYR^{14}$, $(CH_2)_nNR^{12}R^{13}$, $(CH_2)_nCONR^{12}R^{13}$, $(CH_2)_nNCONR^{12}R^{13}$, and $(CH_2)_nCSNR^{12}R^{13}$;
$R^4$, $R^5$ and $R^6$ each is a moiety independently selected from the group consisting of hydrogen, cyano, $R^{12}$, $SR^{12}$ and $NR^{12}R^{13}$, $COYR^{14}$, $(CH_2)_nNR^{12}R^{13}$, $(CH_2)_nCONR^{12}R^{13}$, $(CH_2)_nNCONR^{12}R^{13}$, and $(CH_2)_nCSNR^{12}R^{13}$;
$R^{14}$ is hydrogen
Y is selected from the group consisting of a bond, NH, and O; and
n independently is 0, 1, 2, 3 or 4;
or salt thereof.

2. The compound of claim 1 wherein $R^1$ is $NR^9R^{10}$.

3. The compound of claim 1 wherein one or both of $R^9$ and $R^{10}$ is hydrogen.

4. The compound of claim 1 wherein $R^9$ and $R^{10}$ are hydrogen.

5. The compound of claim 1 wherein $R^2$ is $OR^{12}$.

6. The compound of claim 1 wherein $R^{12}$ is a substituted alkyl.

7. The compound of claim 1 wherein $R^{12}$ is a $C_{1-6}$alkyloxy$C_{1-6}$alkyl moiety.

8. The compound of claim 1 wherein n is 1.

9. The compound of claim 1 wherein $R^1$ is $NR^9R^{10}$, one or both of $R^9$ and $R^{10}$ is hydrogen, $R^2$ is $OR^{12}$ and n is 1.

10. A composition comprising the compound of claim 1 and a pharmaceutically acceptable carrier.

11. The composition of claim 10 that is a dry or liquid composition.

12. A method of administration, comprising administering to a subject the composition of claim 10.

13. The method of claim 12 wherein the composition is locally administered.

* * * * *

UNITED STATES PATENT AND TRADEMARK OFFICE
CERTIFICATE OF CORRECTION

PATENT NO. : 8,846,697 B2  
APPLICATION NO. : 12/302738  
DATED : September 30, 2014  
INVENTOR(S) : Carson et al.

Page 1 of 2

It is certified that error appears in the above-identified patent and that said Letters Patent is hereby corrected as shown below:

On the Title Page

On page 4, in column 1, under "Other Publications", line 67, delete "agoinst" and insert --agonist--, therefor In the Specification In column 6, line 6, delete "$C_{3-4}$heteroaryl," and insert --$C_{3-6}$heteroaryl,-- therefor In column 19, Formula IV, delete " 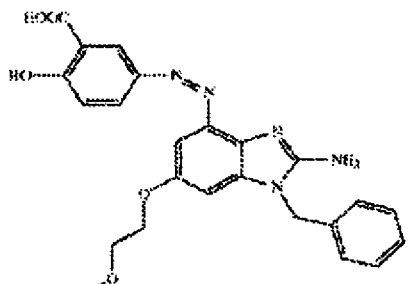 " and insert -- 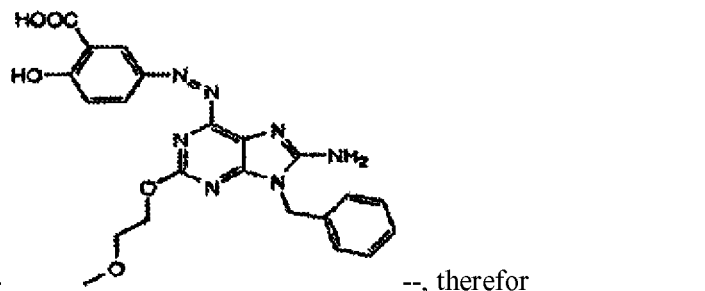 --, therefor Signed and Sealed this  
Thirtieth Day of June, 2015

Michelle K. Lee  
*Director of the United States Patent and Trademark Office*

CERTIFICATE OF CORRECTION (continued)
U.S. Pat. No. 8,846,697 B2

In the Claims

In column 37, line 59, in Claim 1, after "hydrazino", insert --,--, therefor

In column 38, line 1, in Claim 1, delete "$R^{10}$each" and insert --$R^{10}$ each--, therefor